US012788604B2

(12) United States Patent
Showalter et al.

(10) Patent No.: US 12,788,604 B2
(45) **Date of Patent: *Nov. 10, 2026**

(54) ORTHOPEDIC DEVICE PROVIDING METERED TOE TRACTION WITH VARIABLE ADDUCTION, DORSIFLEXION AND ROTATION ANGLES INCLUDING LATERAL GLIDE OF THE FIRST METATARSAL HEAD

(71) Applicants: Christopher Richard Showalter, Southold, NY (US); Christopher John Greetham, Woodbridge, VA (US)

(72) Inventors: Christopher Richard Showalter, Southold, NY (US); Christopher John Greetham, Woodbridge, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/013,027

(22) Filed: Jan. 8, 2025

(65) Prior Publication Data

US 2025/0241778 A1 Jul. 31, 2025

Related U.S. Application Data

(63) Continuation of application No. 18/488,073, filed on Oct. 17, 2023, now Pat. No. 12,213,902, which is a (Continued)

(51) Int. Cl.
*A61F 5/01* (2006.01)
*A61H 1/02* (2006.01)

(52) U.S. Cl.
CPC ............ *A61F 5/019* (2013.01); *A61H 1/0266* (2013.01); *A61H 2001/027* (2013.01); (Continued)

(58) Field of Classification Search
CPC .. A61H 1/0266; A61H 1/0285; A61H 1/0288; A61H 1/0218; A61H 1/0229; (Continued)

(56) References Cited

U.S. PATENT DOCUMENTS

| | | |
|---|---|---|
| 353,910 A | 12/1886 | Zacharie |
| 611,860 A | 10/1898 | Hayward |

(Continued)

FOREIGN PATENT DOCUMENTS

| | | |
|---|---|---|
| DE | 20 2013 102677 U1 | 7/2013 |
| JP | 2010 082408 A | 4/2010 |

OTHER PUBLICATIONS

James Cyriax and Margaret Coldham, Textbook of Orthopedic Medicine, vol. Two, Treatment by Manipulation, Massage and Injection, 11th Ed., Bailliere Tindall, 1984, p. 255.

*Primary Examiner* — Rachael E Bredefeld

(74) *Attorney, Agent, or Firm* — Thomas A. O'Rourke; James Bongiorno; O'Rourke IP Law, PLLC

(57) ABSTRACT

An apparatus applies traction to a digit of a patient's foot at a desired adduction angle and a desired dorsiflexion angle, for use in treating a bunion. The apparatus includes: a shoe portion (e.g., a sole, and strap(s)); a digit attachment apparatus (e.g., a Chinese finger trap) having a cable extending therefrom; and an apparatus (e.g., a ratchet, an actuator, and the like) configured to apply tension to the cable with respect to the sole. A support bracket is configured to pivot with respect to the shoe portion to adjust the adduction angle of the cable with respect to an axial direction of the sole, and is further configured to extend upwardly to at an elevated position with respect to the sole. An adjustment member is mounted to slide relative to the support bracket, to adjust the dorsiflexion angle provided by the cable independent of the adduction angle.

5 Claims, 22 Drawing Sheets

Related U.S. Application Data continuation of application No. 17/666,661, filed on Feb. 8, 2022, now Pat. No. 11,819,440, which is a continuation of application No. 15/162,777, filed on May 24, 2016, now Pat. No. 11,278,440.

(60) Provisional application No. 62/172,934, filed on Jun. 9, 2015.

(52) U.S. Cl.
CPC ................. *A61H 2201/0119* (2013.01); *A61H 2201/1215* (2013.01); *A61H 2201/1409* (2013.01); *A61H 2201/1436* (2013.01); *A61H 2201/164* (2013.01); *A61H 2201/1642* (2013.01); *A61H 2201/1645* (2013.01); *A61H 2201/1671* (2013.01); *A61H 2201/5061* (2013.01); *A61H 2201/5071* (2013.01)

(58) Field of Classification Search
CPC ................ A61H 1/00; A61H 2001/027; A61H 2001/0207; A61H 2001/0288; A61F 5/04; A61F 5/042; A61F 5/05; A61F 5/10; A61F 5/37; A61F 5/3761; A61F 5/3769; A61F 5/019
USPC ................................... 602/36, 30, 31, 22, 21
See application file for complete search history.

(56) References Cited

U.S. PATENT DOCUMENTS

| | | | | |
|---|---|---|---|---|
| 643,068 | A | 2/1900 | Pond | |
| 892,412 | A | 7/1908 | Farra | |
| 1,012,017 | A | 12/1911 | Salt | |
| 1,055,810 | A | 3/1913 | Scholl | |
| 1,213,786 | A | 1/1917 | Wilms | |
| 1,268,932 | A | 6/1918 | Corrigan | |
| 1,340,700 | A | 5/1920 | Dahl | |
| 1,402,375 | A | 1/1922 | Parisi | |
| 1,650,603 | A | 11/1927 | Burton | |
| 1,746,865 | A | 2/1930 | Page | |
| 1,784,032 | A | 12/1930 | Stern | |
| 1,867,679 | A | 7/1932 | Riehle | |
| 1,996,614 | A | 4/1935 | Davis | |
| 2,033,609 | A | 3/1936 | Budin | |
| 2,099,401 | A | 11/1937 | Jungmann | |
| 2,146,933 | A * | 2/1939 | Budin | A61H 1/0218 602/30 |
| 2,190,016 | A | 2/1940 | Day | |
| 2,237,251 | A | 4/1941 | Longfellow | |
| 2,335,665 | A | 11/1943 | Goldmerstein | |
| 2,416,823 | A | 3/1947 | Day | |
| 2,438,144 | A | 3/1948 | Bunyar | |
| 2,506,308 | A | 5/1950 | Maynier | |
| 2,584,203 | A | 2/1952 | Hart | |
| 2,596,038 | A | 5/1952 | Mayer | |
| 2,646,794 | A | 7/1953 | Baer | |
| 2,688,961 | A | 9/1954 | Thomas | |
| 2,734,285 | A | 2/1956 | Levitt | |
| 2,740,207 | A | 4/1956 | Starensier | |
| 2,751,693 | A | 6/1956 | Baker | |
| 2,783,758 | A | 3/1957 | Trott | |
| 2,808,662 | A | 10/1957 | Webb | |
| 2,925,734 | A | 2/1960 | Gorgens | |
| 2,958,324 | A | 11/1960 | Berkemann | |
| 2,969,221 | A | 1/1961 | Harmes | |
| 3,049,120 | A | 8/1962 | Marcus | |
| 3,063,446 | A | 11/1962 | Levitt | |
| 3,066,678 | A | 12/1962 | Riecken | |
| 3,109,314 | A | 11/1963 | Morisawa | |
| 3,139,884 | A | 7/1964 | Stryker | |
| 3,219,032 | A | 11/1965 | Levitt | |
| 3,275,002 | A | 9/1966 | Scholl | |
| 3,390,675 | A | 7/1968 | Giannestras | |
| 3,693,617 | A | 9/1972 | Trott | |
| 3,850,166 | A | 11/1974 | Tamny | |
| 3,872,861 | A | 3/1975 | Tamny | |
| 3,998,429 | A | 12/1976 | Cheung | |
| 4,207,880 | A | 6/1980 | Zinkovich | |
| 4,244,359 | A | 1/1981 | Dieterich | |
| 4,263,902 | A | 4/1981 | Dieterich | |
| 4,318,533 | A | 3/1982 | Port | |
| 4,393,876 | A | 7/1983 | Dieterich | |
| 4,542,883 | A | 9/1985 | Rutzki | |
| 4,563,787 | A | 1/1986 | Drew | |
| 4,583,303 | A | 4/1986 | Laiacona | |
| 4,637,381 | A | 1/1987 | Jungmann | |
| 4,644,940 | A | 2/1987 | Nakamura | |
| 4,724,827 | A | 2/1988 | Schneck | |
| 4,729,369 | A | 3/1988 | Cook | |
| 4,741,087 | A | 5/1988 | Plummer | |
| 4,809,688 | A | 3/1989 | Aymerica del Valle | |
| 4,813,162 | A | 3/1989 | Harris | |
| 4,819,644 | A | 4/1989 | Cherniak | |
| 4,869,499 | A | 9/1989 | Schiraldo | |
| 4,966,167 | A | 10/1990 | Jacobs | |
| 5,027,802 | A | 7/1991 | Donohue | |
| 5,074,291 | A | 12/1991 | Carter | |
| 5,103,536 | A | 4/1992 | Kamper | |
| 5,154,692 | A | 10/1992 | Lockhart | |
| 5,282,782 | A | 2/1994 | Kasahara | |
| 5,437,616 | A | 8/1995 | Kasahara | |
| 5,441,480 | A | 8/1995 | Kane | |
| 5,451,203 | A | 9/1995 | Lamb | |
| 5,453,083 | A | 9/1995 | Kashahara | |
| 5,649,541 | A | 7/1997 | Stuckey | |
| 5,735,806 | A | 4/1998 | Leibovic | |
| 5,928,173 | A | 7/1999 | Unruh | |
| 5,943,742 | A | 8/1999 | Huang | |
| 6,093,163 | A | 7/2000 | Chong | |
| 6,315,749 | B1 | 11/2001 | Sunayama | |
| 6,467,487 | B1 | 10/2002 | Rios | |
| 6,533,743 | B1 | 3/2003 | Moss | |
| 6,629,943 | B1 | 10/2003 | Schroder | |
| 6,758,827 | B2 | 7/2004 | Moss | |
| 6,784,799 | B2 | 8/2004 | Hsien | |
| 6,811,541 | B2 | 11/2004 | Lambert | |
| 6,964,645 | B1 | 11/2005 | Smits | |
| 7,055,268 | B2 | 6/2006 | Ha | |
| 7,131,939 | B2 | 11/2006 | Ferri | |
| 7,374,152 | B2 | 5/2008 | Ruan | |
| 7,383,089 | B2 | 6/2008 | Demian | |
| 7,396,338 | B2 | 7/2008 | Huber | |
| 7,596,887 | B2 | 10/2009 | McClellan | |
| 7,703,218 | B2 | 4/2010 | Burgess | |
| 7,794,417 | B1 | 9/2010 | Zimmerman | |
| 8,277,459 | B2 | 10/2012 | Sand | |
| 8,413,349 | B2 | 4/2013 | Krauss | |
| 8,535,390 | B1 | 9/2013 | Lecomte | |
| 8,739,434 | B2 | 6/2014 | Bishop | |
| 8,832,971 | B2 | 9/2014 | Heid | |
| 8,870,876 | B2 | 10/2014 | Lettmann | |
| 12,213,902 | B2 * | 2/2025 | Showalter | A61F 5/019 |
| 2012/0310131 | A1 | 12/2012 | Rosen | |
| 2013/0047464 | A1 | 2/2013 | Schuler | |

* cited by examiner

ORTHOPEDIC DEVICE PROVIDING METERED TOE TRACTION WITH VARIABLE ADDUCTION, DORSIFLEXION AND ROTATION ANGLES INCLUDING LATERAL GLIDE OF THE FIRST METATARSAL HEAD

CROSS-REFERENCES

This application is a continuation of U.S. patent application Ser. No. 18/488,073, filed on Oct. 17, 2023, which is a continuation of U.S. patent application Ser. No. 17/666,661, filed on Feb. 8, 2022 and issued as U.S. Pat. No. 11,819,440 on Nov. 21, 2023, which is a continuation of U.S. patent application Ser. No. 15/162,777, filed on May 24, 2016 and issues as U.S. Pat. No. 11,278,440 on Mar. 22, 2022, which claims priority on U.S. Provisional Application Ser. No. 62/172,934 filed on Jun. 9, 2015, all disclosures of which are incorporated herein by reference.

FIELD OF THE INVENTION

The present invention relates to apparatus for treating various conditions of a person's toes, and more particularly to apparatus which are capable of providing a measured amount of traction to a toe, which may be adjusted in terms of traction force and adduction, dorsiflexion, and medial and lateral rotation angles, in addition to lateral glide of the head of the first metatarsal head angle.

BACKGROUND OF THE INVENTION

There are many medical problems that affect the toes of a person's feet. A common problem is known colloquially as a bunion, and is termed Hallux Abducto Valgus within the medical community. Hallux Valgus, also known as "Jaccoud's Arthropathy," is characterized by progressive deterioration of the first metatarsal (MT) joint of the great (big) toe.

Normal great, or big toe alignment is characterized by a Hallux Valgus Angle (HVA) of between 5 and 10 degrees of the long axis of the proximal phalanx bone of the toe relative to the long axis of the metatarsal bone at the metatarsophalangeal (MTP) joint. (Hart et al 2008). A clinical diagnosis of Hallux Valgus is made when this angle exceeds 15 degrees. The first phase of the disorder involves modest lateral drifting of the great toe (greater than 20 degrees) towards the other toes. This phase is accompanied by early stage inflammation and swelling, which may go unnoticed as it is often relatively painless. However, the patient may begin to notice the lateral drift, but the resultant aesthetic loss is minor.

The second phase begins with reddening and puffiness of the skin over the metatarsal head. The skin soon becomes inflamed and scar tissue forms. The resulting bunion makes wearing narrow toed shoes, and many other types of shoes, painful if not impossible. The second phase is also characterized by mild to moderate pain, stiffness (hypomobility) of the metatarsal phalangeal joint (MTP) and further lateral drift of the great toe (HVA>30 degrees). The deformity becomes very noticeable, and patients tend to find it acutely embarrassing.

The third phase is characterized by increasing lateral drift (HVA>40 degrees—see FIG. 2) and further deformity. The bunion becomes large and painful, and the toe becomes even more hypomobile (i.e., stiff), having a diminished range of motion in all directions due to scarring and decreased activity. The big toe may also suffer from arthritis. The drift deformity is now extreme and shoe options are severely limited to very wide toe box shoes, which are decidedly unfashionable. Walking is painful and the patient often seeks surgical intervention at this point.

It is generally agreed that certain inherited foot traits—flat feet, excessive ligamentous flexibility, abnormal bone structure, and some nerve conditions—may tend to make a person more susceptible to developing bunions, which is evidenced by appearance of the deformity in younger individuals. However, hallux valgus is most prevalent in women from western cultures, particularly women over the age of 35. So, while experts may be divided on whether ill-fitting footwear may be attributable as being the principle cause of bunions, it is agreed that the problem is at least exacerbated by prolonged wearing of high heeled, narrow toe box shoes. It may also be precipitated or compounded by foot injuries. Studies show that bunions are less prevalent in individuals who tend to go barefoot, while women are 10 time more likely to develop bunions than are men, with this disparity lending further weight as to the causation/exacerbation being attributable to the tendency of women to wear high-heeled, narrow-toes shoes. Bunions are also quite common for ballet dancers—individuals who are often plagued by foot injuries, and who also regularly wear tight leather or canvas slippers.

Current non-surgical treatment options now generally include custom-made orthoses. However, a recent report shows that these "appear to have no effect in the evolution of mild and moderate HV during a 12 month period . . . " Reina M, Lafuente G, and Munuera P V, "*Effect of Custom-made Foot Orthoses in Female Hallux Valgus After One-year Follow Up*," Prosthetics and Orthotics International, April 2013; 37(2):113-9.

Another treatment option includes the use of custom insoles with toe separators (night splints), however studies have shown that the use of a "night splint seems to have no effect on painful hallux valgus deformity," and "was not effective in improvement of the great toe angles . . . " Tehraninasr A, Saeedi H, Forogh B, Bahramizadeh M, and Keyhani M R, "*Effects of Insole with Toe-Separator and Night Splint on Patients with Painful Hallux Valgus: A Comparative Study*," Prosthetics and Orthotics International, March 2008; 32(1):79-83.

Treatment for a severe deformity may include surgery. However, before a deformity progresses to the severity that may only be countered with corrective surgery, treatment nonetheless calls for the use of an orthopedic device. The present invention provides an improved orthopedic device that may be used for the treatment of hallux valgus, as well as other for other conditions (i.e., hammer toe, mallet toe, and claw toe).

OBJECTS OF THE INVENTION

It is an object of the invention to provide an orthotic device capable of placing one or more toes of a patient's foot in traction.

It is another object of the invention to provide an orthotic device in the form of a shoe.

It is also object of the invention to provide a measured amount of traction to the patient's toe or toes.

It is a further object of the invention to provide traction to one or more toes of the patient and to be capable of adjusting the adduction, dorsiflexion, rotation angles thereto, and further capable of providing a lateral glide to the head of the metatarsal.

It is another object of the invention to provide an orthotic device that the patient may be capable of independently applying and wearing without the assistance of a medical practitioner.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In accordance with at least one embodiment of the present invention, a device for use in placing a toe of a patient's foot in traction may broadly include a shoe portion; a toe attachment apparatus (e.g., a Chinese finger trap, a finger stall, and the like); a cable having a first end and a second end, the first end of the cable coupled to the toe trap; a pulley, with the cable configured to wrap about the pulley; and an apparatus (e.g., a ratchet, an actuator that may be pneumatic, with a pressure gauge, and the like) configured to apply tension to the cable to create traction in the toe.

The device may also include an actuator that may be configured to adjust lateral positioning of the pulley relative to the shoe portion to set a desired angle of adduction for the traction provided to the toe by the cable. The device may also include a meter coupled to the cable and configured to indicate an amount of tension provided thereto by the ratchet. The device may further include a second actuator configured to adjust elevational positioning of the pulley relative to the sole of the shoe portion to set a desired angle of dorsiflexion for the traction provided to the toe by the cable. Where a ratchet is used to apply tension to the cable, the wheel of the ratchet may be configured to receive a tool to actuate the ratchet. The wheel of the ratchet may have a fine set of teeth formed thereon to allow for small adjustment to be made to the tension in the cable. The shoe portion of the device may broadly include a sole; a counter configured to brace the back of the patient's foot; and one or more straps configured to secure the patient's foot within the shoe portion, to brace the foot with respect to the counter, using hook and loop materials (or a buckle) on the one or more straps.

BRIEF DESCRIPTION OF DRAWINGS

The description of the various example embodiments is explained in conjunction with the following appended drawings.

DETAILED DESCRIPTION OF THE INVENTION

As used throughout this specification, the word "may" is used in a permissive sense (i.e., meaning having the potential to), rather than the mandatory sense (i.e., meaning must). Similarly, the words "include", "including", and "includes" mean including but not limited to.

The phrases "at least one", "one or more", and "and/or" are open-ended expressions that are both conjunctive and disjunctive in operation. For example, each of the expressions "at least one of A, B and C", "one or more of A, B, and C", and "A, B, and/or C" mean all of the following possible combinations: A alone; or B alone; or C alone; or A and B together; or A and C together; or B and C together; or A, B and C together.

Also, all references (e.g., patents, patent application publications, and non-patent literature) that are cited within this document are incorporated herein in their entirety by reference.

Furthermore, the described features, advantages, and characteristics of any particular embodiment disclosed in the following specification, may be combined in any suitable manner with any of the other embodiments disclosed herein.

Figure 2:
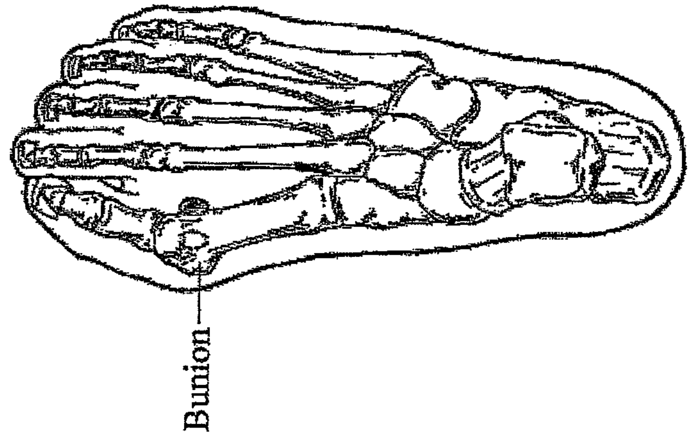
FIG. 2 is a top view of the bones of a foot that is affected by hallux valgus, resulting in an outward facing deformation of the big toe.
Figure 1:
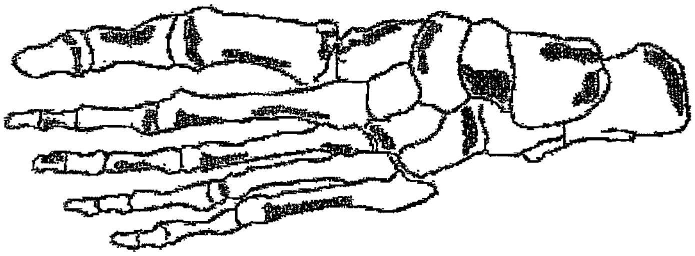
FIG. 1 is a top view of the bones of a normal foot.
Figure 3:
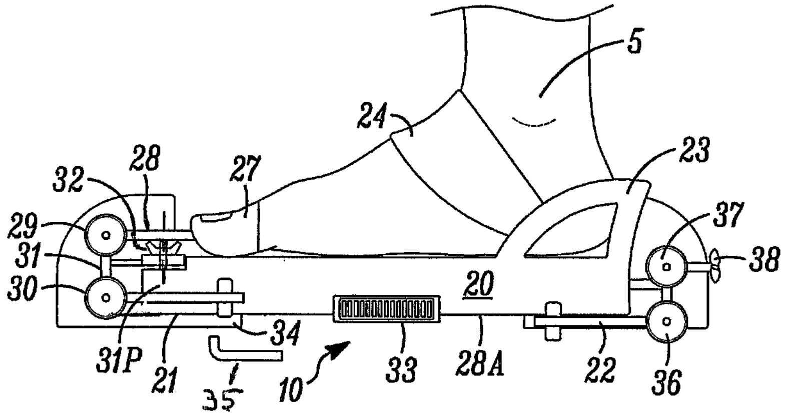
FIG. 3 is a side view of a first embodiment of a toe traction device of the present invention, which is capable of providing traction to a patient's toe using an adjustment of various angles of the toes.

FIG. 3 shows a side view of a toe traction shoe/device 10 of the present invention. It should be noted at the outset that each embodiment of the apparatus described herein is configured to be secured to the patient's foot, and several embodiments being compactly configured may closely resemble a shoe or sandal. However, although it may be possible, the patient would not likely be walking about while wearing the device to applying traction to one of his/her toes. Therefore, throughout this document, the terms "shoe" and "device" are used interchangeably, without intending to detract from the advantageously compact configuration of those particular shoe-like embodiments.

Toe traction shoe 10 may include a sole portion 20, which may extend from a first end 21 to a second end 22. Extending upwardly from the second end 22 of the sole 20 may be a counter 23 that may be used to brace the back of the foot 5. One or more straps may be used to secure the foot 5 within the shoe 10, to brace the foot with respect to the sole to permit traction to be applied to one of the toes. In this embodiment, a single strap 24 may be used to secure the foot with respect to the counter 23. One end of the strap 24 may be fixedly connected to a first side of the shoe 10, and the other end of the strap may be adjustably connected to a second side of the shoe using Velcro® (i.e., respective hook and loop fastening materials), or using a buckle, or using any other securing means known in the art. Alternatively, two straps may be used, where each strap has a first end fixedly connected to a respective side of the shoe, and the second ends of the straps are releasably coupled together using the Velcro materials (e.g., 224Vh and 224VL in FIG. 9).

To treat a hallux valgus condition, traction would necessarily be applied to the big toe. Therefore, without intending this specification to be so limiting, the remainder of the discussion is directed to applying traction to the big toe. However, it may be understood that the present invention may furthermore be constructed and adjusted to be utilized for applying traction to any one, or more, of the different toes of a patient's foot.

A toe of the patient's foot (e.g., the big toe) may receive an attachment means thereon, which may be used for applying tension to that toe. The attachment means may simply be a first string (or a cable, elastomeric member, rubber band, etc.), and a second such string or member being secured to opposite sides of the toe using medical tape. The attachment means may also be in the form of the "Extension Bandage" taught by U.S. Pat. No. 1,268,932 to Corrigan. The attachment means may also be any one of the devices/finger traps taught by U.S. Pat. No. 2,688,961 to Thomas, U.S. Pat. No. 3,872,861 to Tamny, and U.S. Pat. No. 5,451,203 to Lamb, and the like. The "Finger Trap" of the '861 patent to Tamny may be used on the toes of the patient herein, as it is known to simply be a plurality of strands braided together in a substantially cylindrical form, so that when the end of a central strand or strands is pulled, it results in a contraction of the diameter of the cylinder and clamping upon the digit of the patient.

The toe trap 27 shown in FIG. 3 may terminate in a single strand or cable 28, which when pulled may cause contraction of the trap upon the toe of the patient. The strand 28 may wrap around a first pulley 29 to be directed downwardly, and may then wrap around part of a second pulley 30, to be directed rearward with respect to shoe 10. The pulleys 29 and 30 may each be rotatably mounted to a support bracket 31 that may protrude forward of the shoe 10. The strand 28 may be coupled to a tension meter, which may be used to indicate the amount of traction being applied to the toe of the patient. Such tension meters are shown, for example, by U.S. Pat. No. 1,650,603 to Burton, and U.S. Pat. No. 2,925,734 to Gorgens. A ratchet arrangement 34 may be actuated by an Allen key or other tool 35 to add tension to the strand 28. Another strand 28A may couple the other side of the tension meter to a geared tensioning handle 38, with the strand being directed thereto by pulleys 36 and 37, each of which may be rotatably mounted to another support bracket. The handle 38 may be turned to add tension in the cables 28 and 38. Rather than a geared tensioning handle, the handle may be coupled to a screw actuator that may adjust the positioning of the end of the cable with respect to pulley 37 (e.g., rotating the handle to decrease tension, and counter-rotating to increase tension). The actuator may be a screw actuator, such as the actuator shown in any of U.S. Pat. No. 2,831,363 to Lohr, U.S. Pat. No. 3,128,634 to Eastman, U.S. Pat. No. 5,154,091 to Bianco, U.S. Pat. No. 6,321,611 to Szu; or may be a hand-operated pneumatic actuator, such as the one shown by U.S. Pat. No. 5,980,528 to Salys, and the like.

Figure 5:
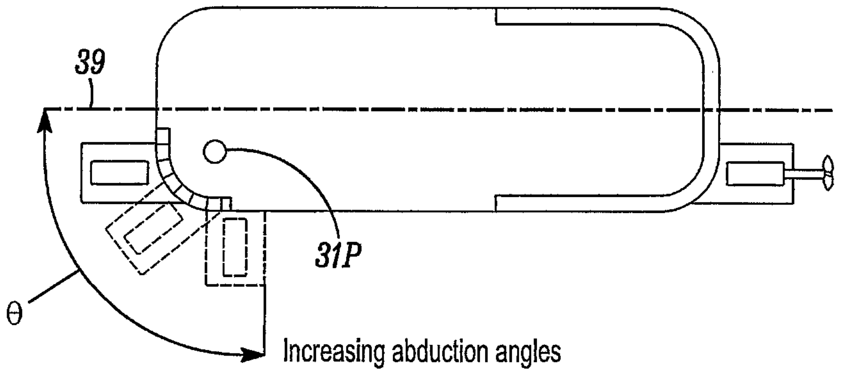
FIG. 5 is a bottom view of the device of FIG. 3.

The support bracket 31, to which pulleys 29 and 30 are rotatably mounted, may itself be pivotally mounted to the sole 20 of shoe 10 at axis 31P (FIGS. 3 and 5). The support bracket 31 may be releasably secured at a suitable angular θ with respect to an axial direction 39 (lengthwise direction) of the shoe, to provide a desired adduction angle for the traction applied to the toe. The angular orientation of the bracket 31 may be releasably secured using a wing nut 32. Matching radial serrations may also be used on the bracket 31 and the sole 20, to reduce the torque that may be needed for the wing nut 32 to releasably secure the bracket to the sole, particularly at greater abduction angles.

Figure 4:
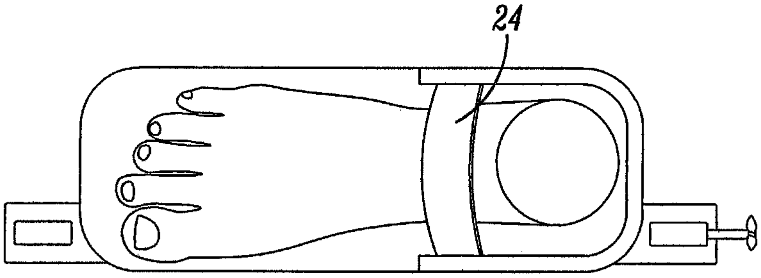
FIG. 4 is a top view of the device of FIG. 3.
Figure 6:
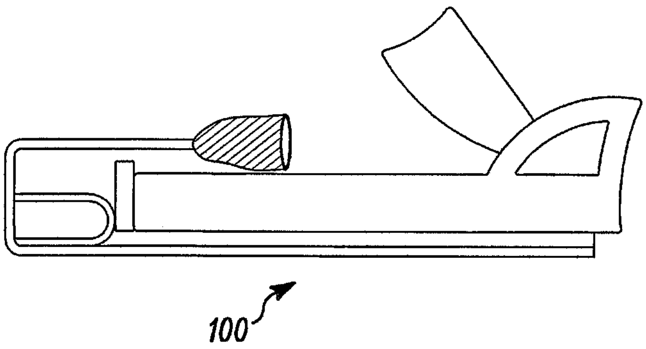
FIG. 6 is a side view of an alternate embodiment of the toe traction device of FIG. 3.
Figure 7:
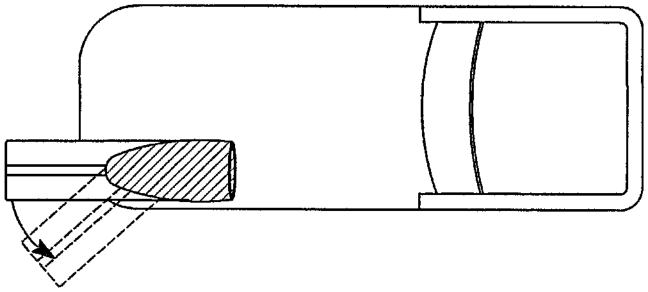
FIG. 7 is top view of the device of FIG. 6.
Figure 8:
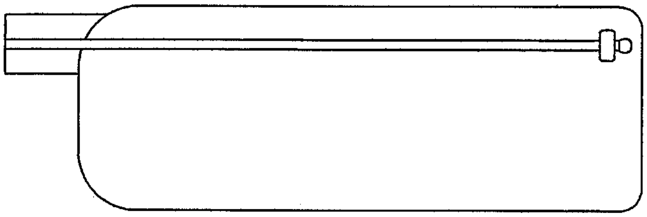
FIG. 8 is a bottom view of the device of FIG. 6.

FIGS. 6-8 show a shoe embodiment 100 constructed similar to the embodiment of FIGS. 3-5, but which does not utilize the tension meter.

Figure 9:
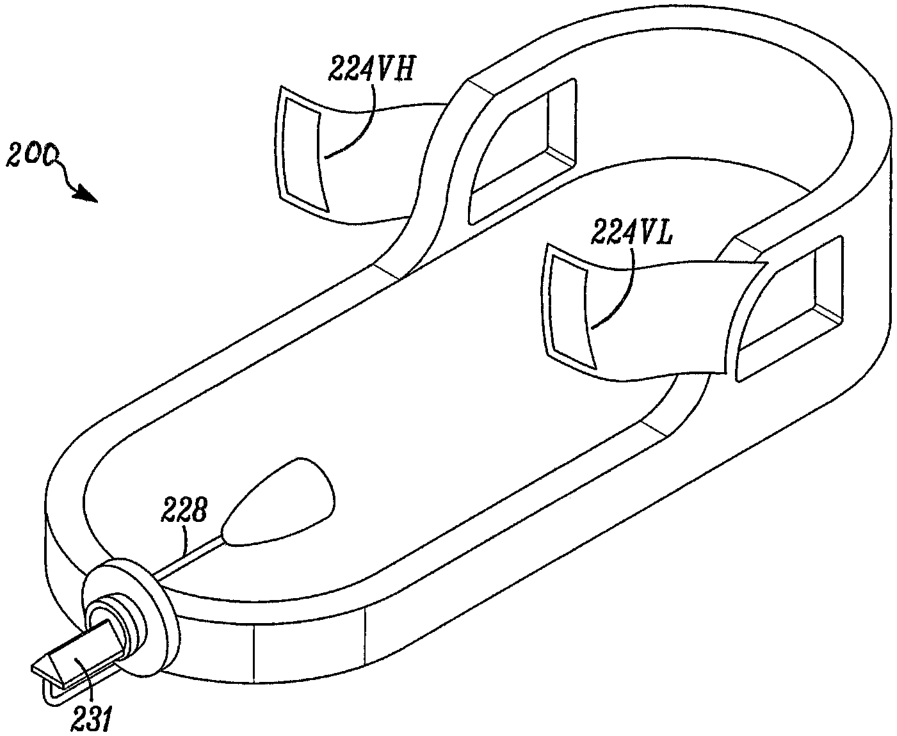
FIG. 9 is a perspective view of an alternate embodiment of the toe traction device of FIG. 6.
Figure 10:
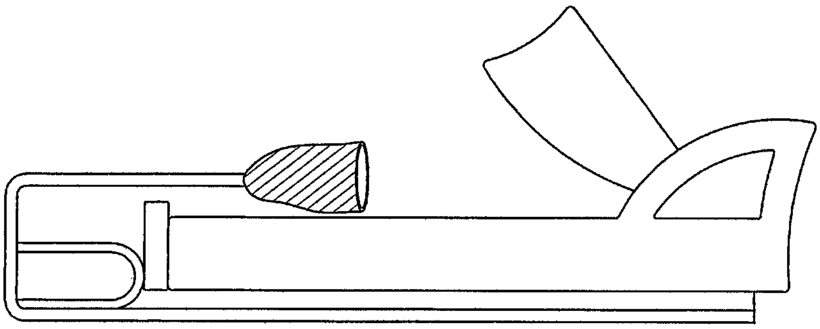
FIG. 10 is a side view of the device of FIG. 9.

FIGS. 9-10 show a shoe embodiment 200 of the present invention constructed similar to the embodiment of FIGS. 6-8, in which a universal joint 231 is utilized to permit more complex adjustments to the orientation of the strand 228. The universal joint may be the same as, or be similar to, the universal joint taught by U.S. Pat. No. 5,062,730 to Tomii.

Figure 11:
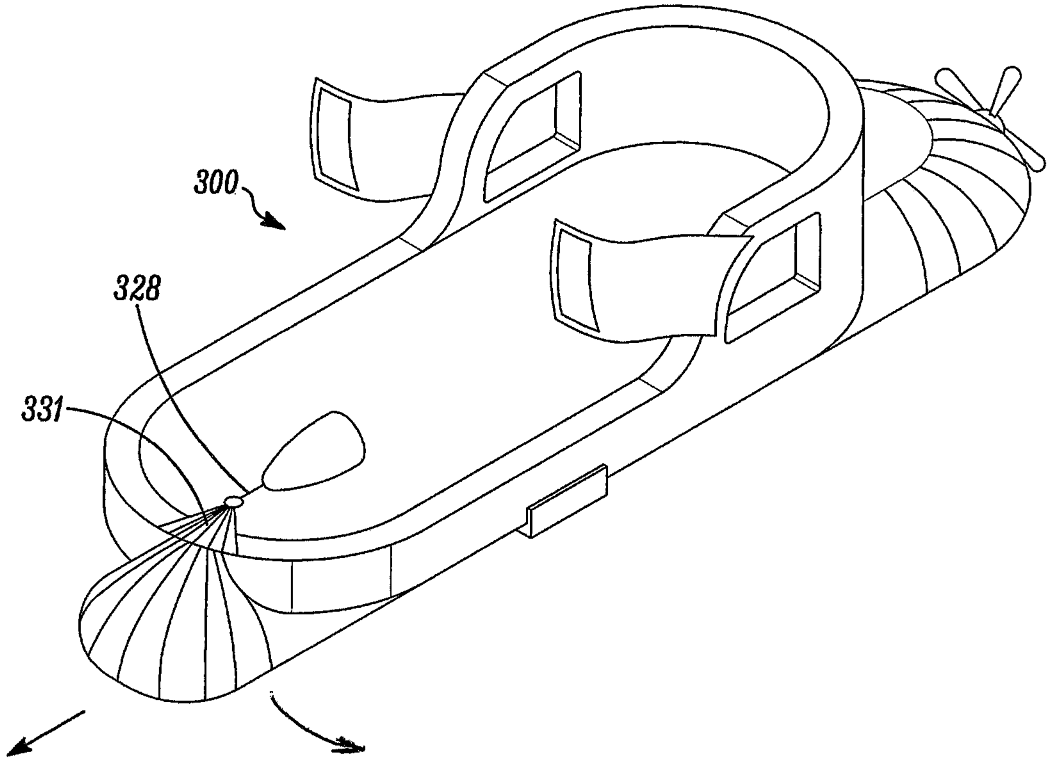
FIG. 11 is a perspective view of an alternate embodiment of the device of FIG. 9.

FIG. 11 shows a shoe embodiment 300 of the present invention constructed similar to the embodiment of FIGS. 3-5, in which a universal joint 331 is utilized to permit more complex adjustments to the orientation of the strand 328. The universal joint may be the same as, or be similar to, the universal joint taught by U.S. Pat. No. 5,062,730 to Tomii.

Figure 12:
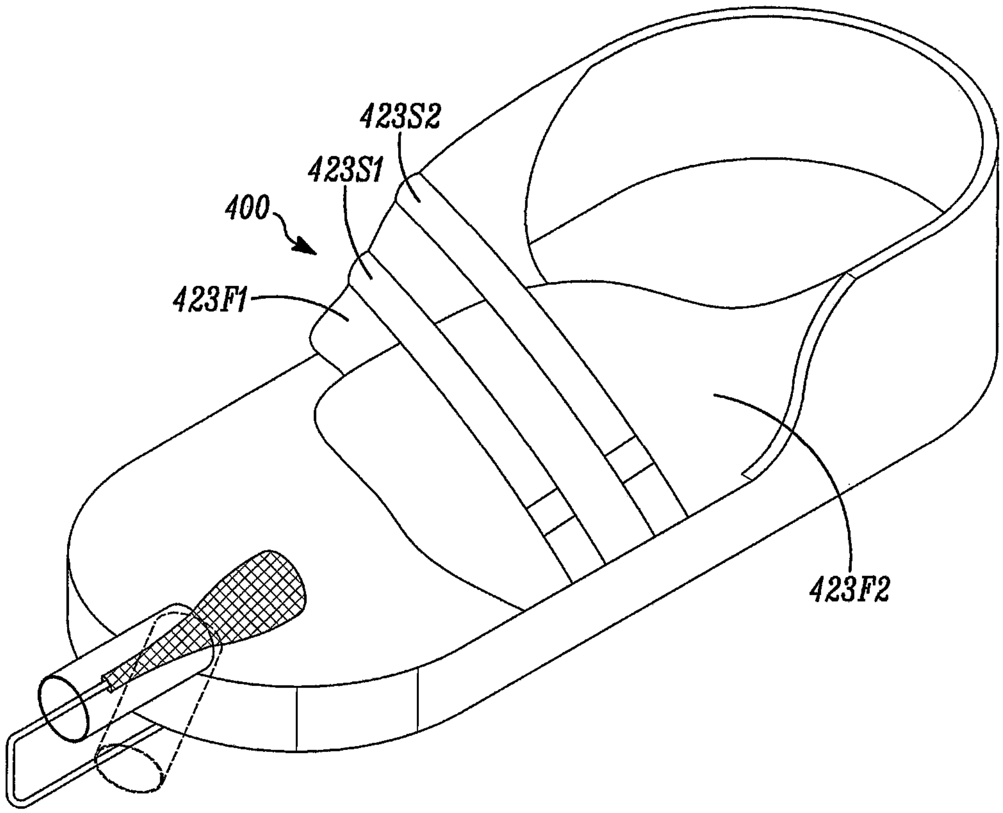
FIG. 12 is a perspective view of an alternate embodiment of the device of FIG. 11.
Figure 13:
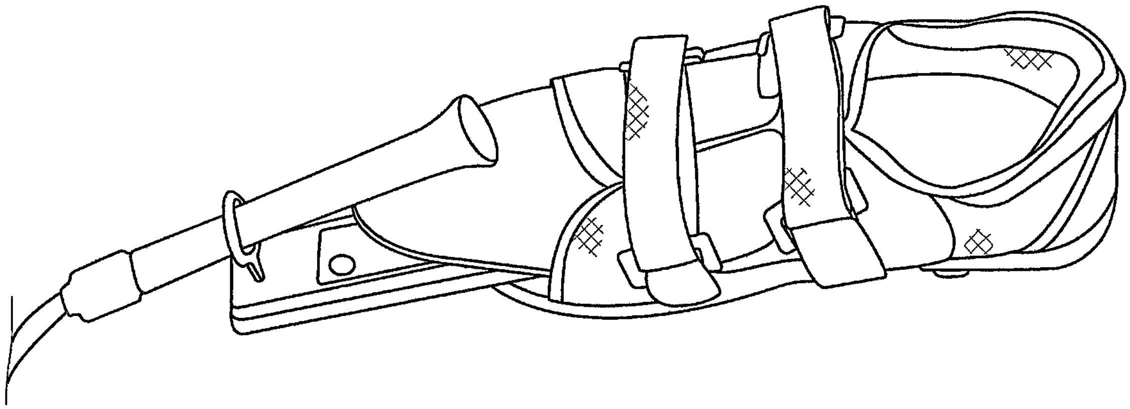
FIG. 13 is a photograph showing a perspective view of a prototype of a toe traction device of the present invention.
Figure 14:
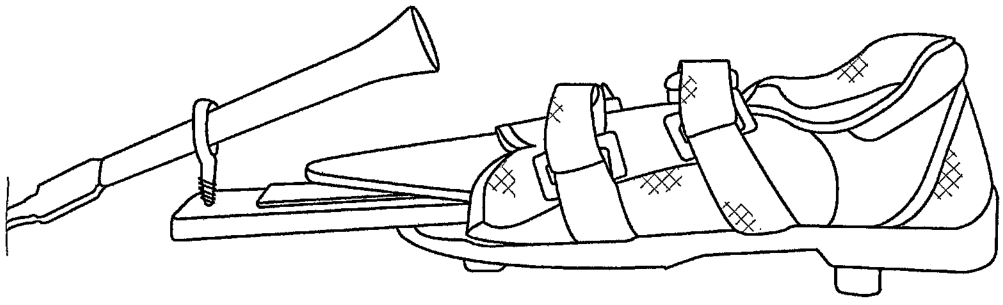
FIG. 14 is a photograph showing a side view of the prototype traction device of FIG. 13.
Figure 15:
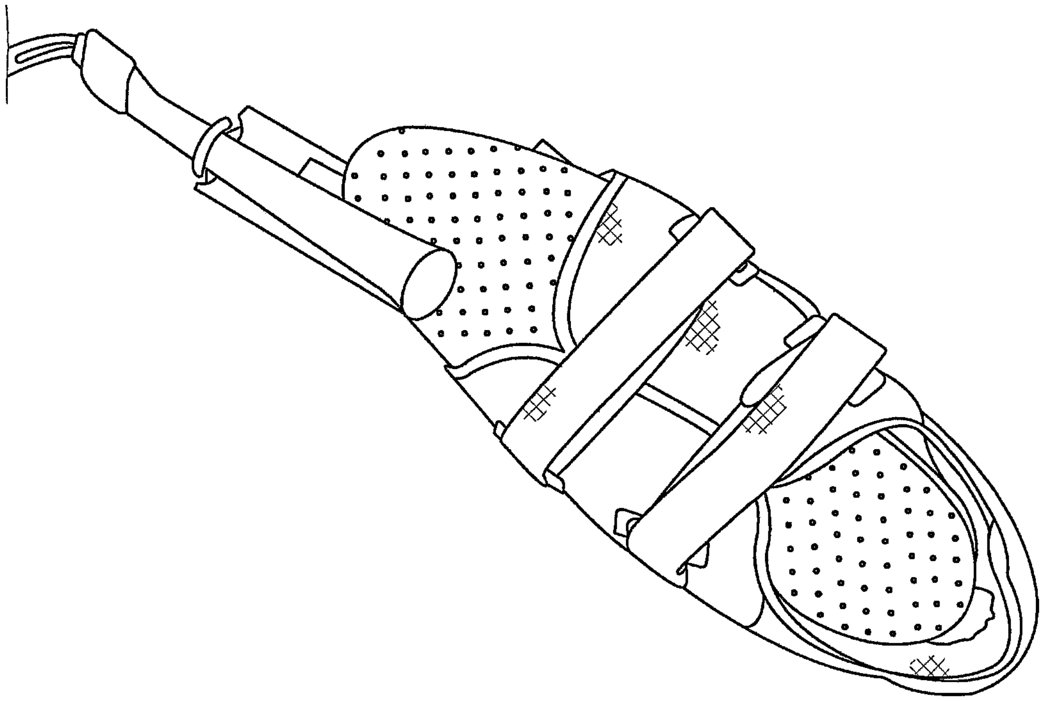
FIG. 15 is a photograph showing a top view of the prototype traction device of FIG. 13.

FIG. 12 shows a shoe embodiment 400 of the present invention, in which a pair of flaps (423F1 and 423F2)—one extending from each side of the shoe—and a pair of top straps 423S1 and 423S2 may be used to secure the shoe with respect to the top of the patient's foot. The straps 423S1 and 423S2 may be releasably coupled across to the other side of the shoe using Velcro.

Figure 16:
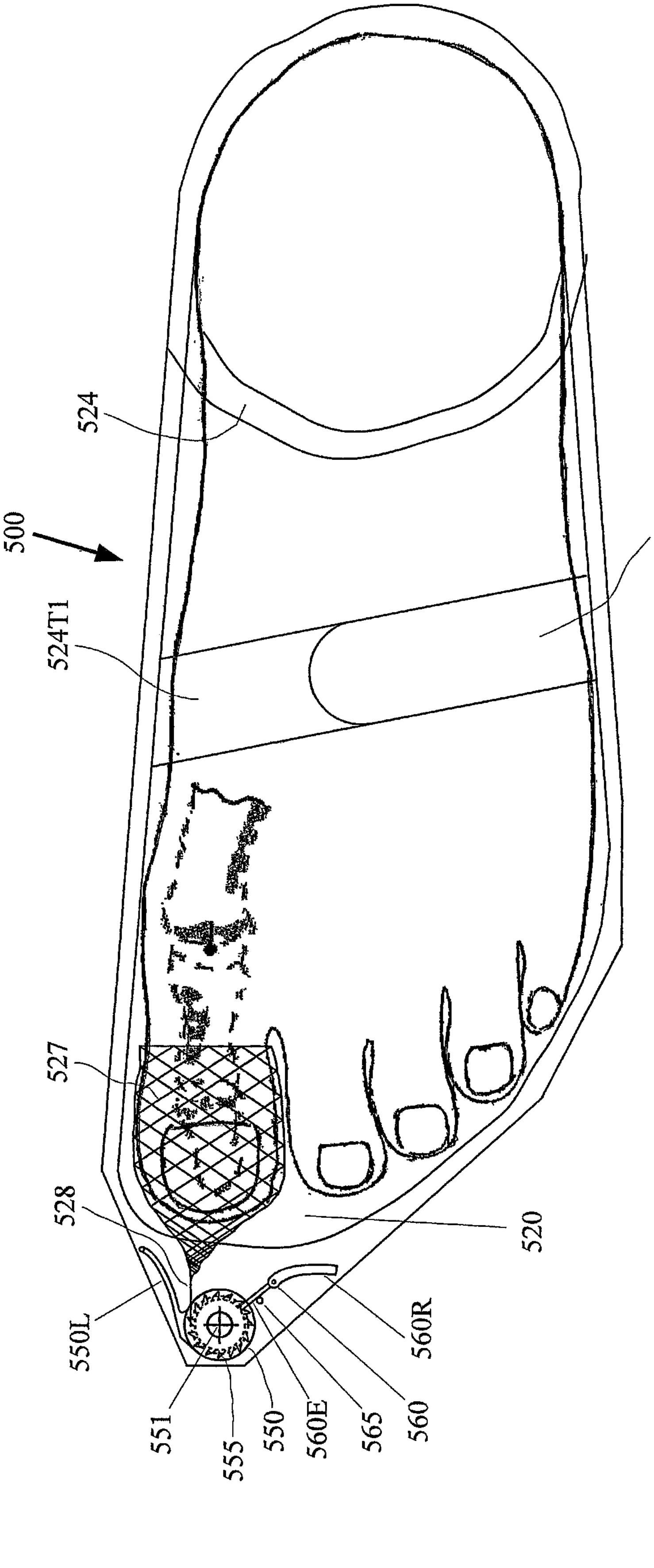
FIG. 16 is a top view of an embodiment of a toe traction device of the present invention.

FIG. 16 shows a shoe embodiment 500 of the present invention that may compactly incorporate hardware components into a front portion of the shoe, to accomplish traction of a toe therein. Shoe 500 may have one or more ankle straps 524 and one or more top straps (e.g., 524T1 and 524T2), to secure the patient's foot within the shoe, the top of which may otherwise be generally open. Shoe 500 may have a spool 550 rotatably mounted at 551 to the sole 520. The end of strand 528 of the toe trap 527 may be coupled to the spool 550, so that rotation of the spool may cause the strand to slowly be coiled thereon, and increase the traction force applied to the toe. Incremental increases in the traction force from the coiling of the strand 528 on the spool 550 may be accommodated by the use of the ratchet arrangement similar to the one disclosed by U.S. Pat. No. 3,109,314 to Morisawa.

A toothed ratchet wheel 555 may be concentrically mounted to the spool 550. Clockwise movement of the spool may generally be prevented by a release arm 560. The release arm 560 may be pivotally mounted to the sole 520 of the shoe, and its engagement end 560E may engage any one of the teeth of the ratchet wheel 555, and may be prevented from clockwise rotation, along with the ratchet wheel, by contact with stop 565, which may protrude up from the sole 520. A torsion spring may normally bias the engagement end 560E of the release arm 560 into contact with the stop 565.

A finger actuable lever 550L may extend from one side of the spool 550. A patient's finger may thereby apply a force to the lever 550L so that it may be moved away from the toe, to cause joint rotation of the spool 550 and ratchet wheel 555, so that the curved (cam) side of one or more successive teeth of the ratchet wheel may drive the engagement end 560E of the release arm 560 to pivot counterclockwise, and incrementally increase the tension in the strand 528. This increased tension in the strand 528 would cause an increase in the traction force applied to the toe. Once the force is removed from lever 550L, the tension in the strand 528 would cause the spool and ratchet wheel to rotate clockwise, which may occur only briefly, until the flat side of the nearest tooth of the ratchet wheel engages with the engagement end 560E of the release arm 560 and causes it to rotate clockwise until contacting stop 565.

The diameter of the spool that takes up (i.e., coils) the strand 528 may be smaller than the diameter at which the lever 550L is coupled thereto, to step down the take up thereby provided. This may permit for very small changes in the amount of the strand that is taken up by the displacement of the lever 550L, so that small incremental increases in traction may be provided to the patient's toe. This would also require a significant plurality of teeth on the ratchet wheel, to accommodate the small incremental changes to the strand tension/toe traction force.

It may be desirable to apply up to approximately 10 kilograms (22 pounds) of traction force to the toe, so the components of shoe 500 would need to be constructed to safely accommodate the resulting loads. Furthermore, the number of teeth used on the ratchet wheel 555, the root diameter of the teeth, and at least the degree of elasticity that may be inherent to the material utilized for the strand 528, may be coordinated and calibrated so that each successive tooth that may be captured by the engagement end 560E of the release arm 560 may add a small incremental amount of tension to the strand, which may be in the range of 0.1 kilograms to 0.5 kilograms, and may preferably be in the range of 0.2 kilograms (0.55 pounds) to 0.3 kilograms. To accomplish small changes to the tension in the cable, a fine to very fine set of teeth may be used on the ratchet wheel. The effect of the number of teeth formed on the ratchet wheel upon its rotation angle when limited by a pawl may be seen in the following chart:

| | |
|---|---|
| 24 Teeth | 15 Degrees per tooth |
| 36 Teeth | 10 Degrees per tooth |
| 45 Teeth | 8 Degrees per tooth |
| 60 Teeth | 6 Degrees per tooth |
| 72 Teeth | 5 Degrees per tooth |
| 80 Teeth | 4.5 Degrees per tooth |
| 100 Teeth | 3.6 Degrees per tooth |

Therefore, to accomplish small changes to the tension in the cable, the number teeth used on the ratchet wheel may preferably be at least 45 or 60 teeth, and more preferably may be 72 teeth or 80 teeth, and most preferably may be 100 teeth.

After the user has applied traction to the toe for a recommended period of time, and desires to remove the shoe 500, a small force may be applied to lever 550L, being just sufficient so that a tooth of the ratchet wheel 555 no longer engages and drives the engagement end 560E of the release arm 560 into contact with stop 565. The release end 560R of the release arm 560 may then be actuated so that the engagement end 560E of the release arm 560 moves clear of the ratchet wheel 555, and upon releasing of the force applied to the lever 550L, the tension in the strand 528 may thereby be released, and the toe trap 527 may be removed from the patient's toe.

Figure 17:
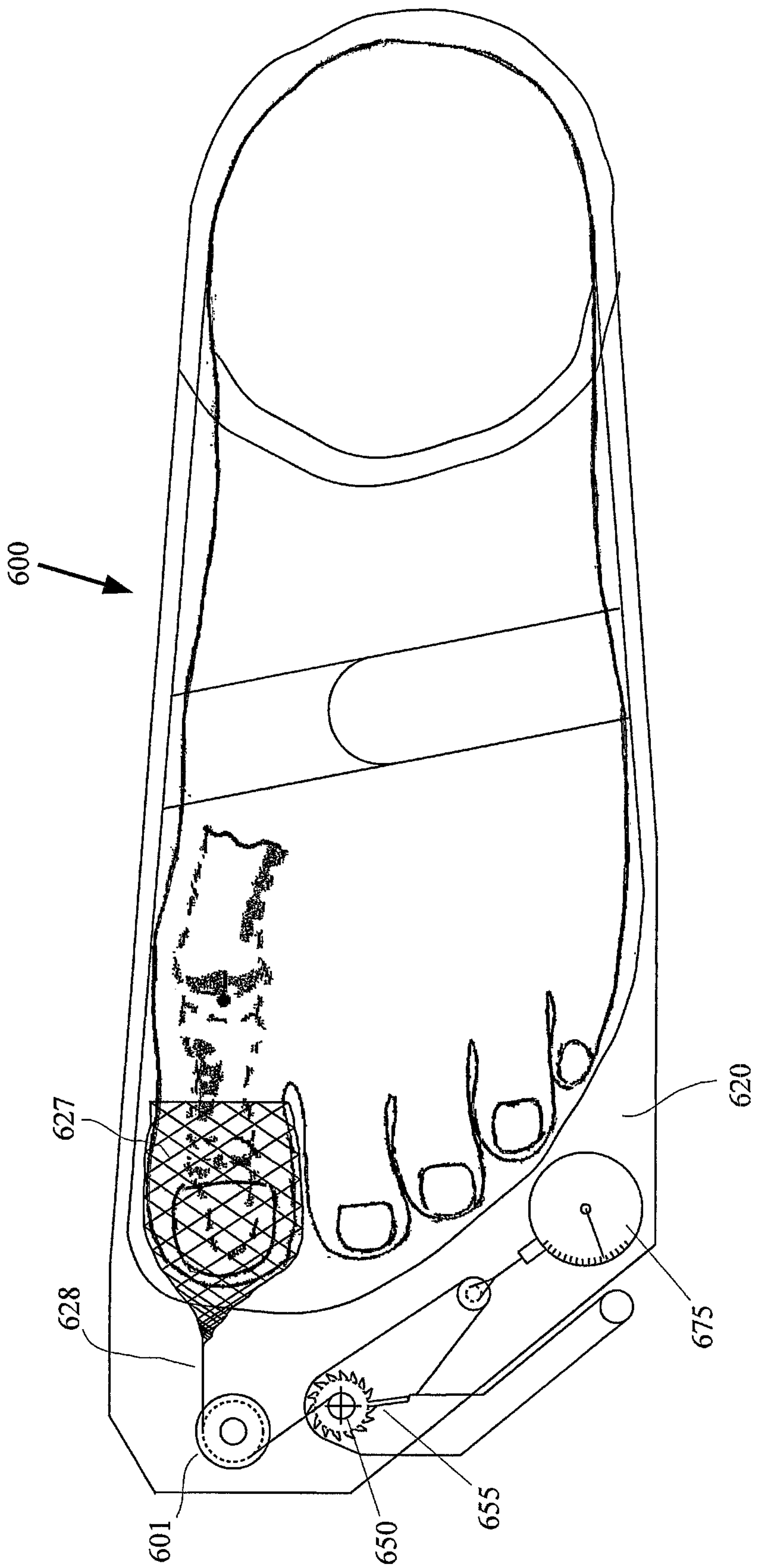
FIG. 17 is a top view of an alternate embodiment of the toe traction device of FIG. 16, which includes a tension meter.

FIG. 17 shows a shoe embodiment 600 of the present invention. For shoe 600, the ratchet wheel and levers 655 may be constructed substantially the same as shown by U.S. Pat. No. 7,374,152 to Ruan. The spool 650 may be positioned the same as it was for shoe 500, or instead, it may be more centrally positioned with respect to the lateral extent of the user's foot, as seen in FIG. 17, and the strand 628 of the toe trap 627 may wrap around a portion of a pulley 601 before being received onto the spool 650 of the ratchet 655. The ratchet 655 for shoe 600 may not be fixedly secured to the sole 620, and instead a tension meter 675 may be fixedly secured to the sole, and a cable may connect an end of the ratchet being distal from the spool 650, with the tension meter. The scale of the tension meter 675 may be oriented so that it may be easily read by the patient seeking to apply traction to his or her toe, or it may be at an orientation that would enable a practitioner to easily read the scale.

Figure 18:
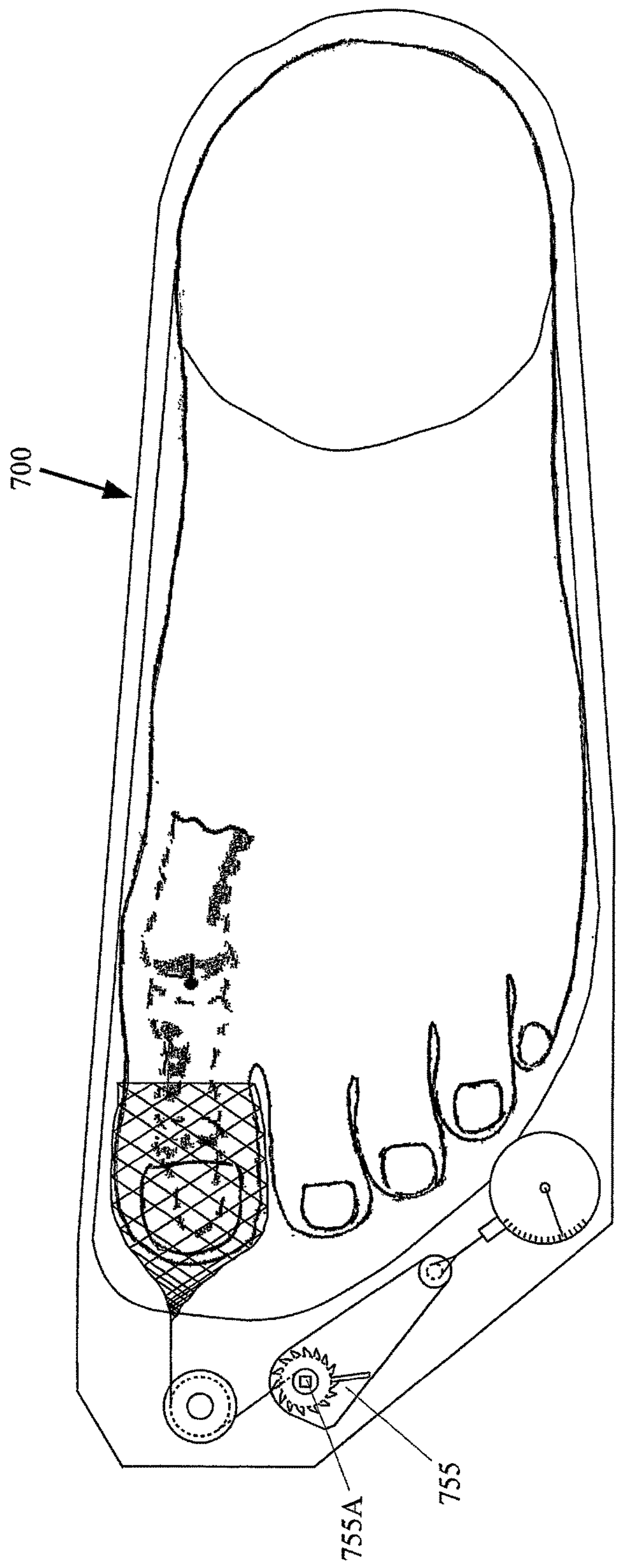
FIG. 18 is a top view of another embodiment of the toe traction device of FIG. 17, in which the ratchet may be driven by a separate removable handle.
Figure 18A:
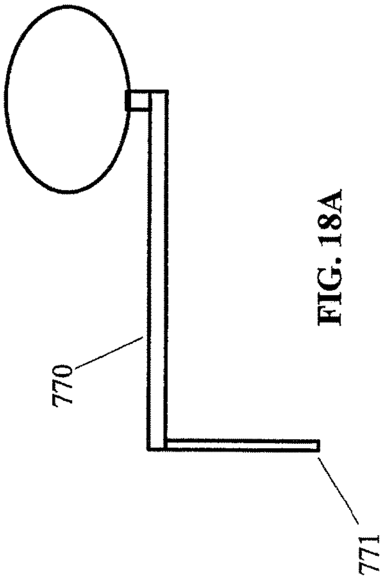
FIG. 18A is a side view of a handle that may be used with the toe traction device of FIG. 18.

FIG. 18 shows a shoe embodiment 700 of the present invention. Shoe 700 may be constructed similar to shoe 600, except that the ratchet assembly may not include an integral handle to actuate the ratchet wheel, and instead, a separate handle 770, as seen in FIG. 18A, may be used. The end 771 of the handle 770 may be inserted into the corresponding opening 755A of the wheel, and the handle may be turned like a crank to actuate the wheel.

Figure 19:
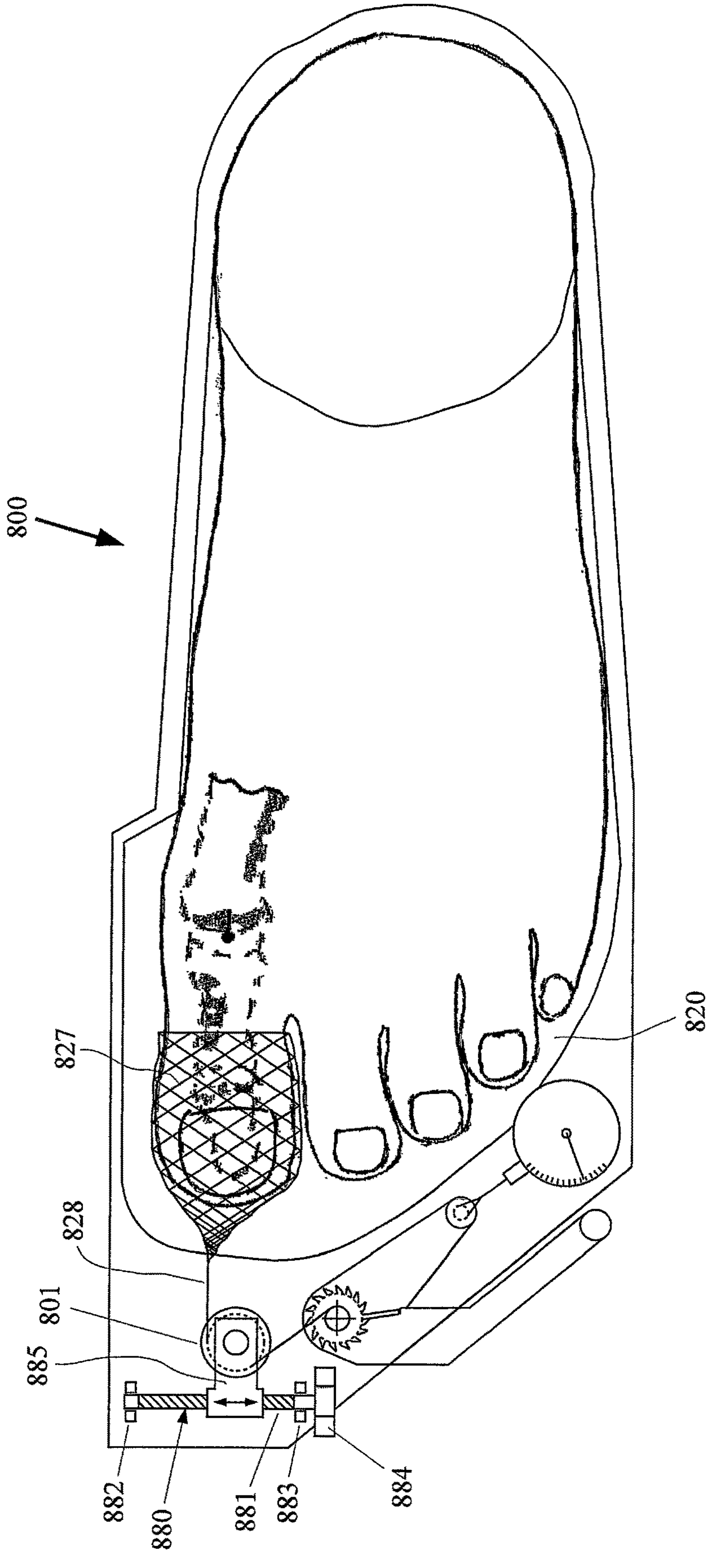
FIG. 19 is a top view of an alternate embodiment of the toe traction device of FIG. 17, in which a linear actuator may be used to adjust an angle of adduction for the traction provided to the toe.

FIG. 19 shows a shoe embodiment 800 of the present invention. Shoe 800 may be constructed similar to shoe 600, except that the pulley 801 may be mounted to an actuator 880, using a universal joint. The actuator 880 may be a ball screw actuator, or any other similar type of actuator configured to provide linear motion, and may be constructed similar to the axial actuator of U.S. Pat. No. 4,938,090 to Brusasco. Actuator 880 may have a shaft 881, the ends of which may be rotatably supported by supports 882 and 883, which may protrude up from sole 820. The shaft may include threading between the supports 882 and 883, and a knob 884 at one end. The knob 884 may be actuated to rotate the shaft 881 to drive the universal joint 885, which may be threadably coupled thereto. The strand 828 being looped about the pulley 801 may prevent the universal point 885 from co-rotating with the rotating shaft 881, so that the relative movement of the threaded connection therebetween may cause translation of the universal joint in a desired direction. This translation may be used to set a desired adduction angle for the tension applied to the toe using the toe trap 827.

Figure 19A:
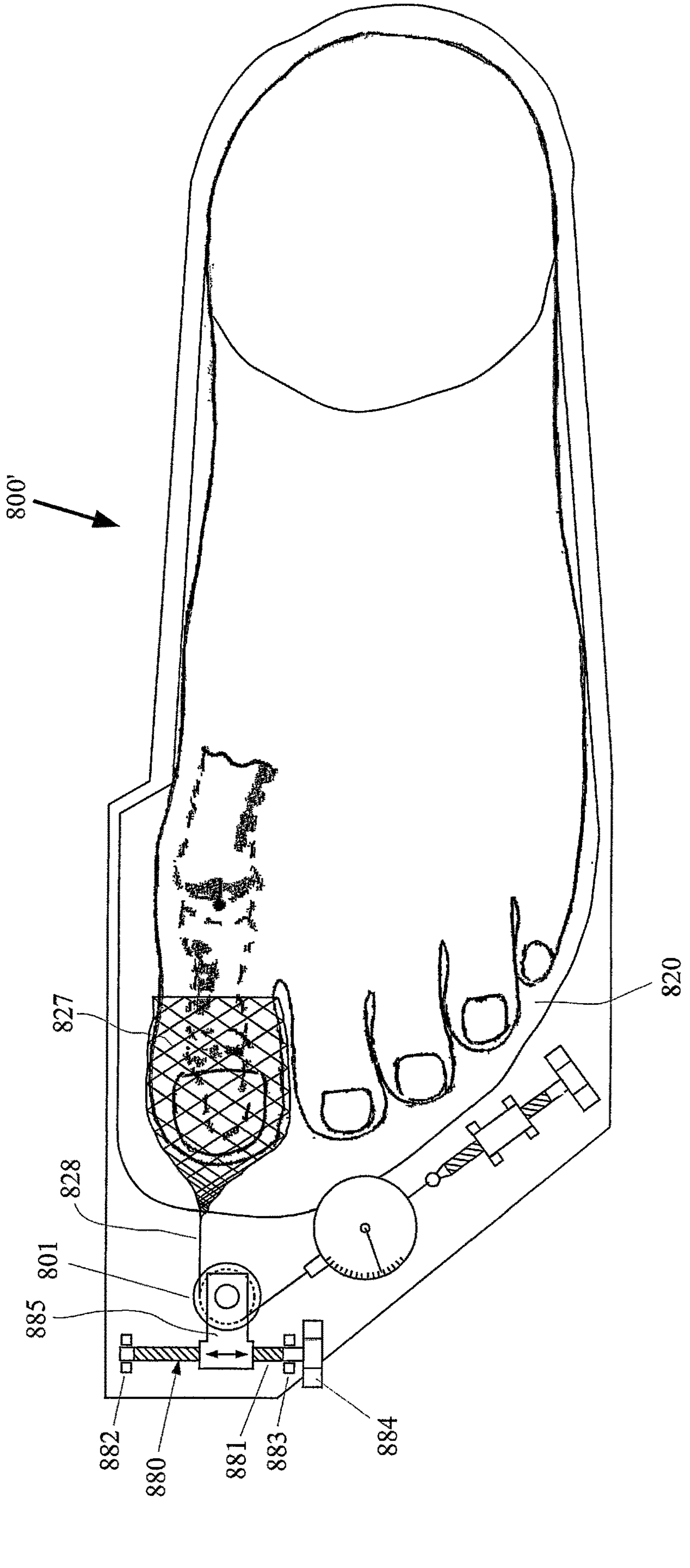
FIG. 19A is a top view of an alternate embodiment of the toe traction device of FIG. 19, in which the ratchet has been replaced with a linear type of actuator.

FIG. 19A shows a shoe embodiment 800' of the present invention. Shoe 800' may be constructed similar to shoe 800, except that rather than using a ratchet to add tension to the cable, the end of the cable (which may include a tension meter) may instead be actuated by a linear actuator (e.g., any of the actuators disclosed herein). The embodiment may provide for a compact arrangement with the cable being directed by the pulley to be at an angle comparable to that formed by at front of the foot, by the decreasing size/positioning of the toes.

Figure 20:
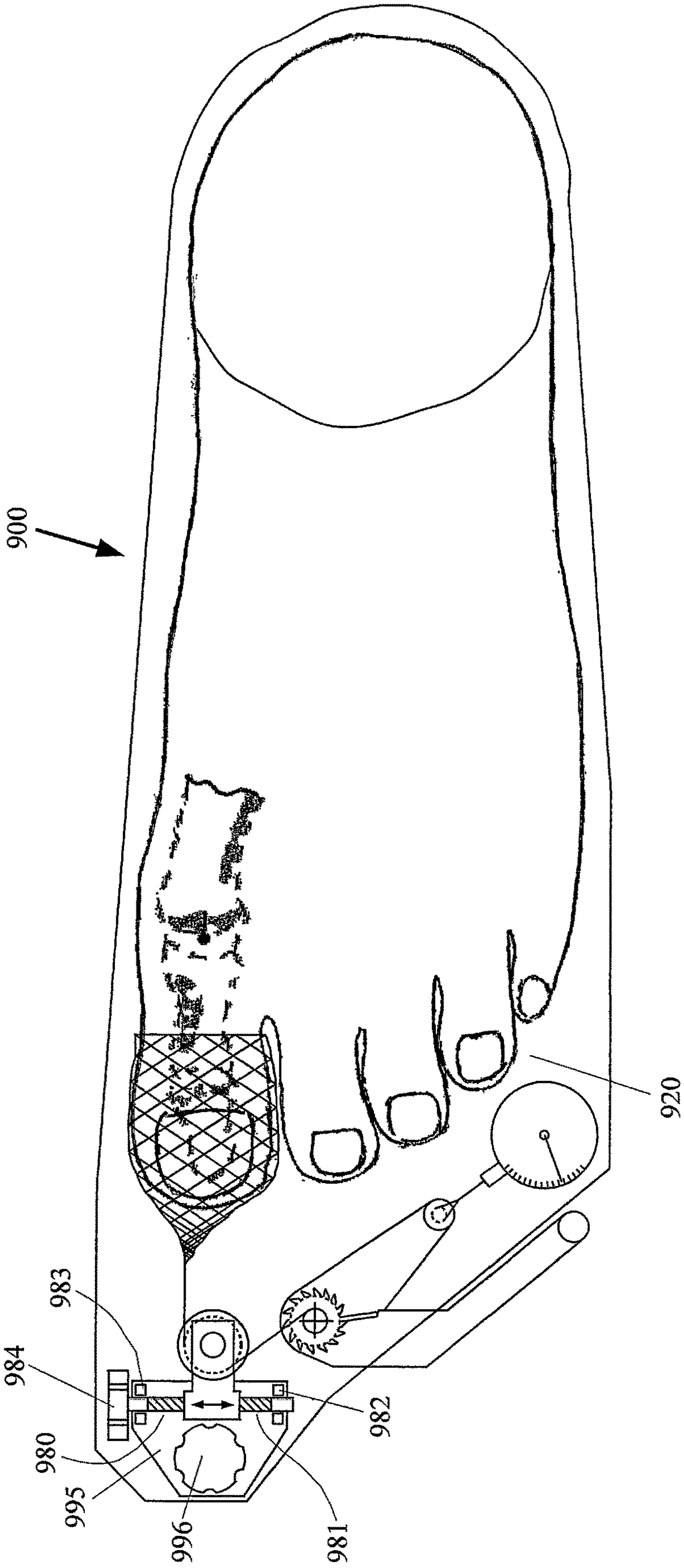
FIG. 20 is a top view of an alternate embodiment of the toe traction device of FIG. 19, in which a second linear actuator may also be used to adjust a height of the device that provides traction to the toe.

FIG. 20 shows a shoe embodiment 900 of the present invention. Shoe 900 may be constructed similar to shoe 800, except that the support posts 982 and 983 that rotatably support the shaft 981 may protrude upward from a plate 995. The plate may be configured to be adjusted up or down with respect to the sole 920 using a second linear actuator 996, to make an elevational adjustment to the pulley relative to the sole, and thereby set a desired dorsiflexion or plantarflexion angle for the traction provided to the toe by said cable.

Figure 21:
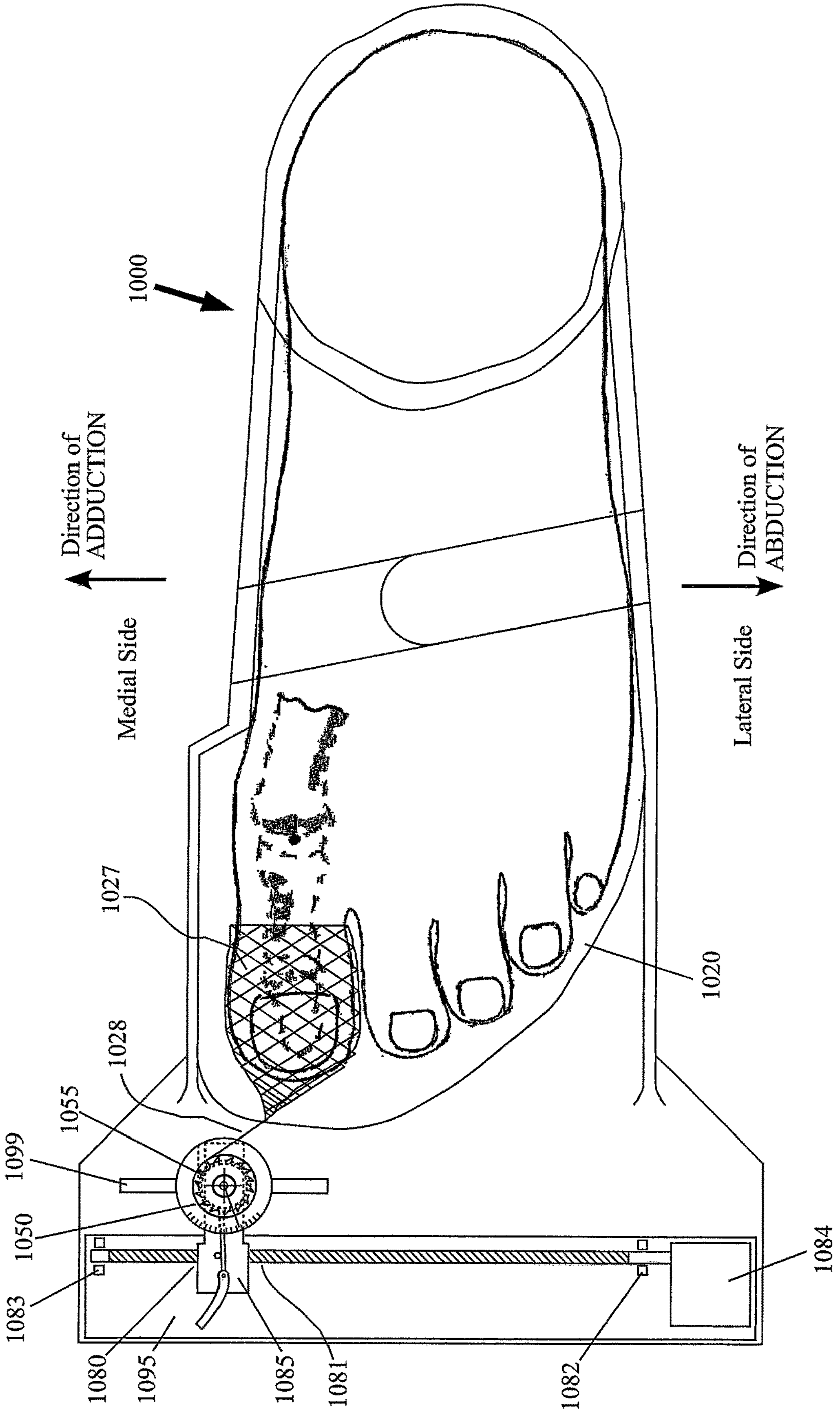
FIG. 21 is a top view of an alternate embodiment of the toe traction device of FIG. 20, in which a metered tension wrench is coupled to the ratchet to provide a direct means for applying a desired amount of traction to the toe.

FIG. 21 shows a shoe embodiment 1000 of the present invention. Shoe 1000 may incorporate aspects of the shoe embodiment 500 shown in FIG. 16, and aspects of the shoe embodiment 900 shown in FIG. 20. As with shoe 500, the shoe 1000 may have a toothed ratchet wheel 1055 concentrically mounted to a spool 1050, except that the ratchet 1055 may be driven by an integral tension wrench 1099 that may be constructed similar to the wrench shown in U.S. Pat. No. 2,256,478 to Hill, which has an integral tension meter upwardly disposed thereon. In addition, rather than manually actuating such a wrench, a rotary actuator may instead be used to precisely apply an amount of torque to the strand 1028 of trap 1027, which produces the desired traction force. The rotary actuator may be constructed in accordance with the teachings known in this art, including, but not limited to, those of U.S. Pat. No. 5,363,025 to Colling for "Actuator Employing Unidirectional Motor for Bidirectional Rotational Positioning; U.S. Pat. No. 5,650,704 to Pratt for "Elastic Actuator for Precise Force Control"; and U.S. Pat. No. 5,368,112 to Mount for "Tensioning Apparatus for Tie Down Lines." In addition, rather than manually actuating the shaft 1081 of the ball screw actuator arrangement to adjust the abduction angle, as with knob 984 for shoe 900, a rotary actuator 1084 may instead be used to move the universal joint laterally in either direction. Furthermore, it should be understood that any of the actuators that may be utilized by this invention may be take any suitable form, and may include, but not be limited to, pneumatic actuators, hydraulic actuators, electric actuators, etc., any of which may include tension gauges thereon.

FIGS. 22-29 show a traction apparatus 1100 of the present invention. Apparatus 1100 may have a plate 1105 to which a shoe 1110 may be fixedly secured. The bottom of the plate 1105 may have one or more platforms 1111 that may be used to elevate the plate above the floor. Although there are only two platforms 1111 shown throughout the figures, additional platforms may also be used, or alternatively, a single platform that may extend around a substantial portion of the periphery of the plate 1105 may instead be used to elevate the plate 1105.

Figure 22:
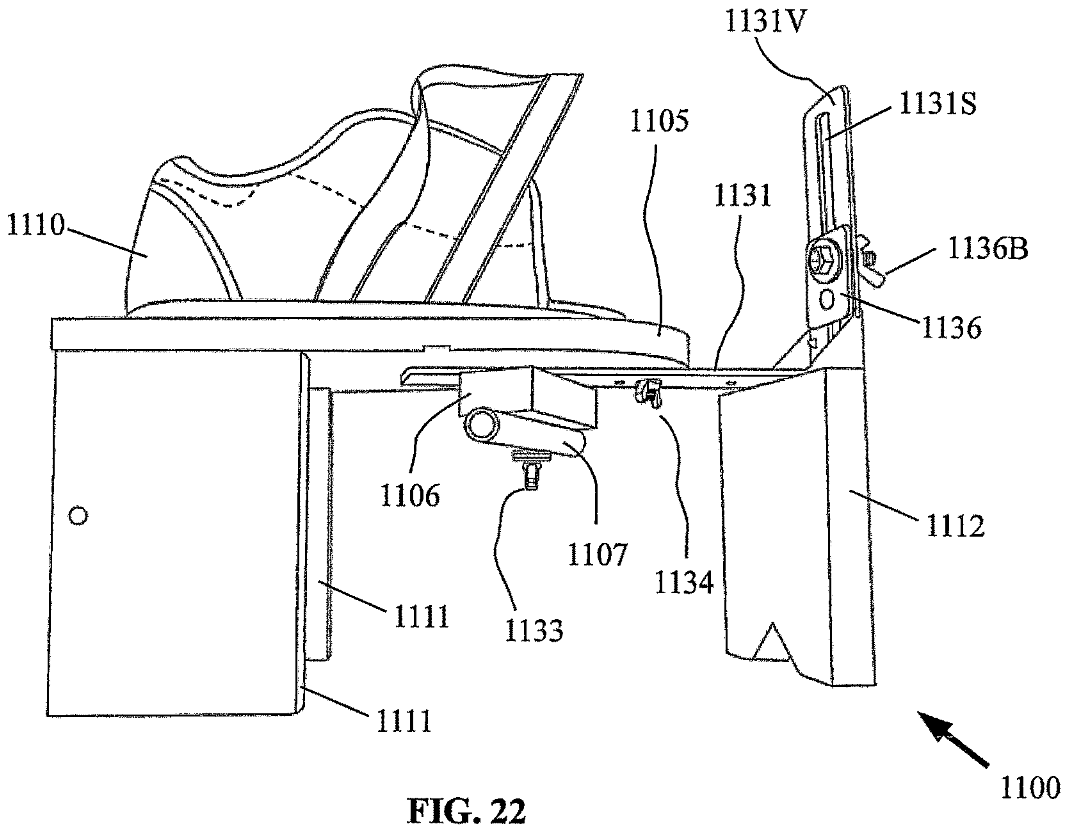
FIG. 22 illustrates a side perspective view of another embodiment of a traction apparatus of the present invention.
Figure 23:
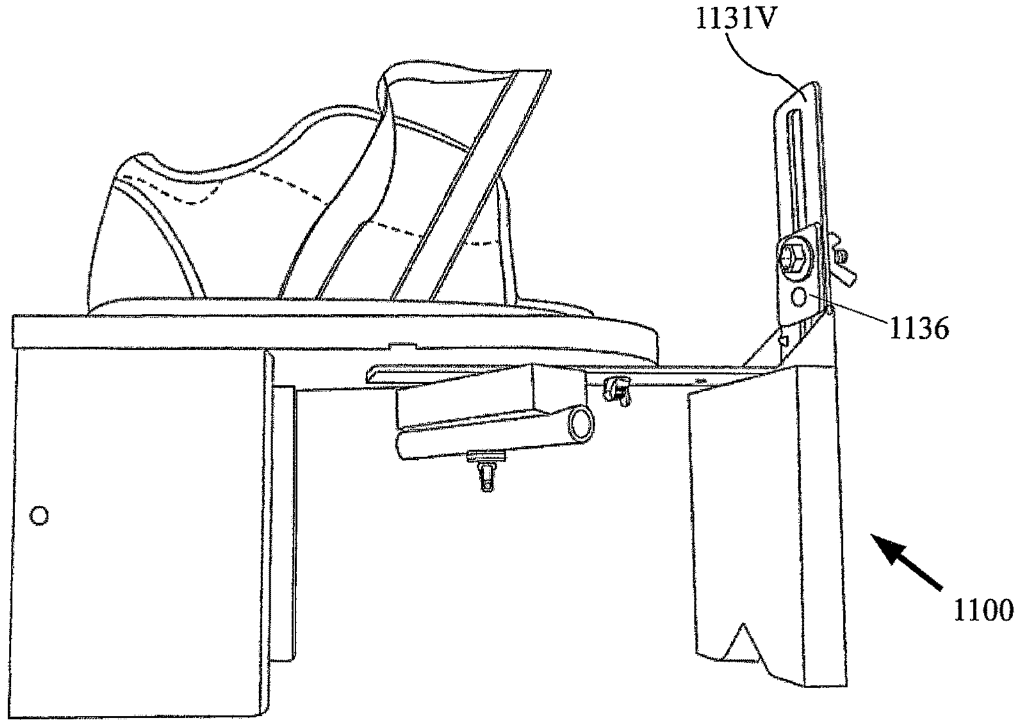
FIG. 23 shows a second side perspective view of the traction apparatus shown in FIG. 22.
Figure 24:
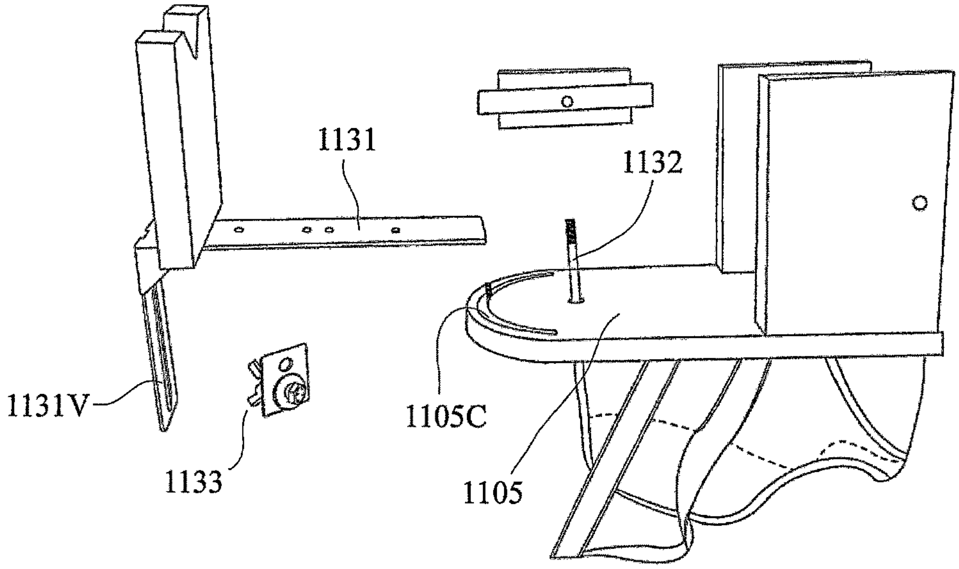
FIG. 24 is an exploded view showing the component parts of the traction apparatus of FIG. 22.
Figure 25:
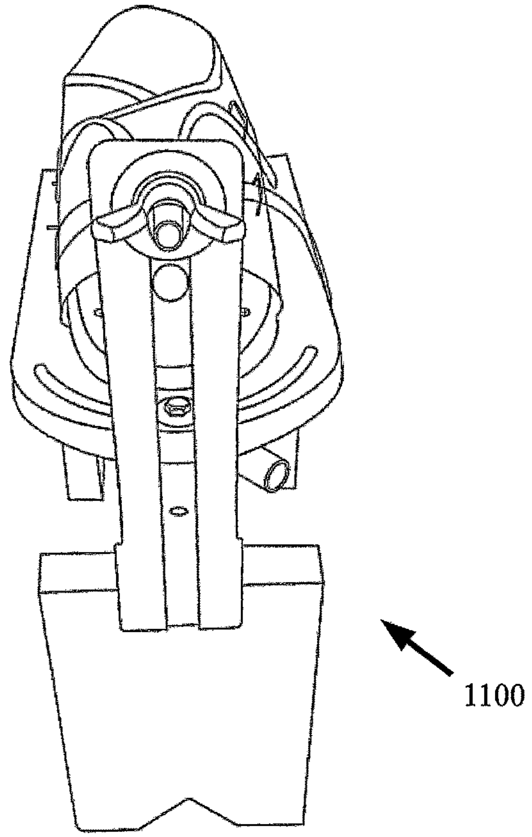
FIG. 25 is a front view of the traction apparatus of FIG. 22.

A support bracket 1131 may be pivotally mounted to the bottom of the plate 1105, using, for example, the rod 1132 shown in the exploded view of FIG. 24. A wing-nut 1133 may be threaded onto the rod to secure the arm 1132 thereto. Applying a sufficient amount of torque to the wing-nut 1133 may also serve to releasably secure the angular orientation of the arm with respect to the shoe. Alternatively, a block 1106 and/or a flexible cylindrical member 1107 may be interposed between the bottom of the plate 1105 and the wing-nut, which may serve to generally allow the arm to remain pivotally secured to the plate, without restricting its angular positioning. In this case, a bolt and a second wingnut combination 1134 may be used to releasably secure the angular positioning of the arm 1131 with respect to the plate 1105, as seen in FIG. 22, with the bolt being received through a semi-circular opening 1105C in the plate 1105, which may be seen in FIG. 24. Instead of the semi-circular opening, a plurality of individual holes may be positioned thereat, which would require removal of the bolt for repositioning of the arm. A secondary platform 1112 (FIG. 22) may be used to support the arm 1131.

Figure 26:
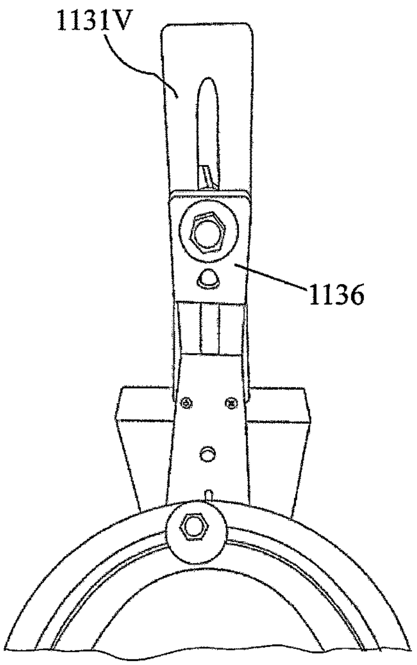
FIG. 26 is a rear view of the forward portion of the traction apparatus of FIG. 22, with the slidable adjustment plate shown at a lower position.
Figure 27:
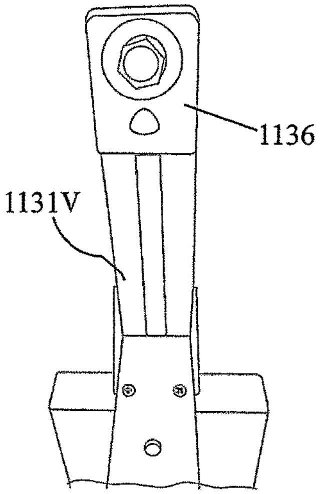
FIG. 27 is a rear view of the forward portion of the traction apparatus of FIG. 22, with the slidable adjustment plate shown at an elevated position.

The arm 1131 may have a 90 degree bend formed therein, to create a vertical arm portion 1131V. The strand of a toe trap may be secured to an adjustment plate 1136, using any of the means previously disclosed herein. A slot 1131S in the vertical arm portion 1131V of the arm 1131 may permit the adjustment plate 1136 to be releasably and adjustably secured thereto using a bolt and a wing-nut combination 1136B. The adjustment plate 1136 may thus be moved and secured to any desired elevated position with respect to the sole of the shoe 1110, to provide for application of traction to the toe at a desired dorsiflexion angle, in addition to a desired adduction angle. The adjustment plate 1136 is shown in FIG. 26 secured at a lower position on the vertical arm portion 1131V of the arm 1131, and is shown at a more elevated position with respect to the vertical arm portion within FIG. 27.

Figure 28:
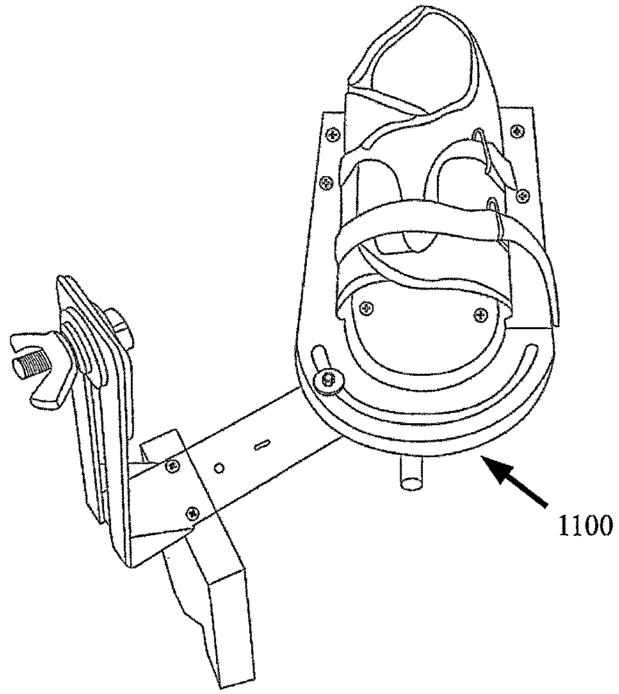
FIG. 28 is a top perspective view of the traction apparatus of FIG. 22, with the arm positioned on a first side of the apparatus.
Figure 29:
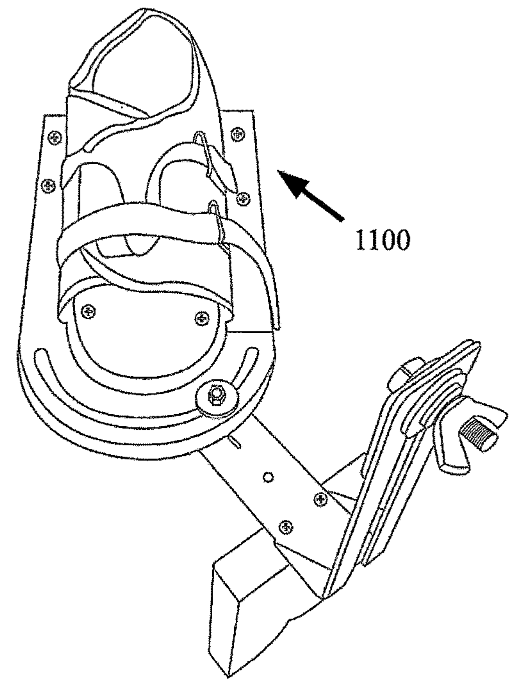
FIG. 29 is the top perspective view of FIG. 28, but shown with the arm positioned on a second side of the apparatus.

This embodiment, as with other embodiments described hereinabove, is not restricted to use for only one foot or the other (i.e., only the left foot, or only the right foot), as the design is universal, and is adjustable for use with either foot, as the arm 1131 may be pivoted and secured to provide a desired adduction angle for any toe for the left foot or the right foot (FIGS. 28-29).

Figure 30:
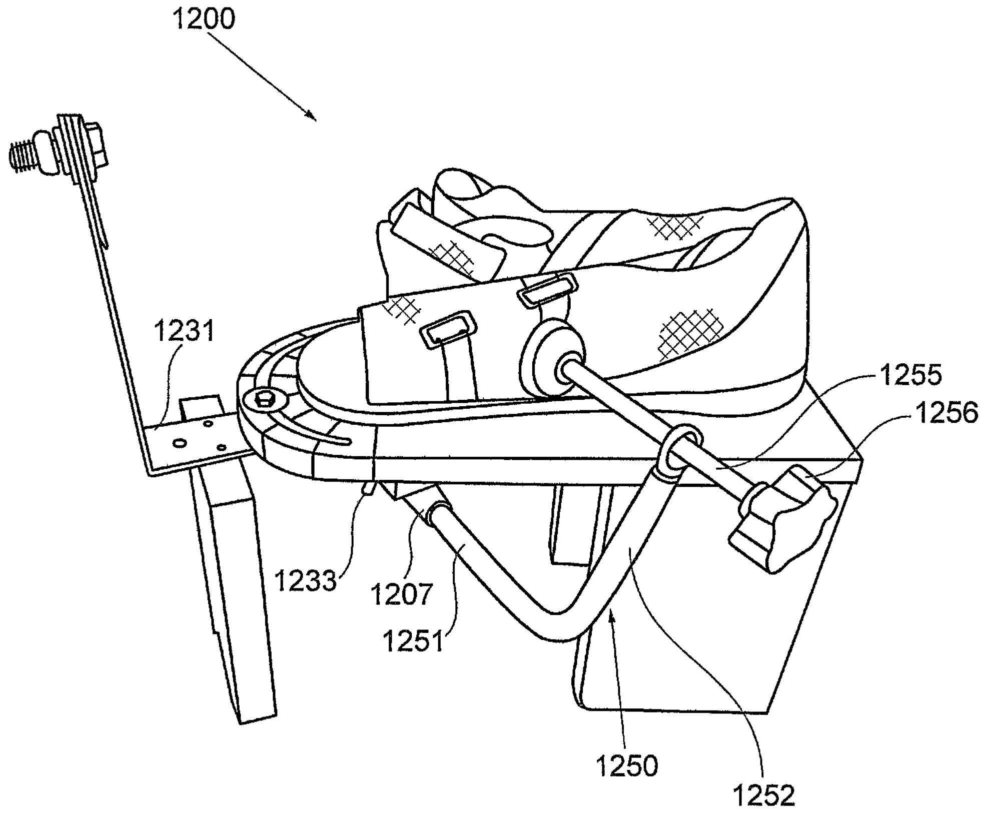
FIG. 30 illustrates a side perspective view of another embodiment of the traction apparatus of FIG. 22, which includes a clamp device.
Figure 31:
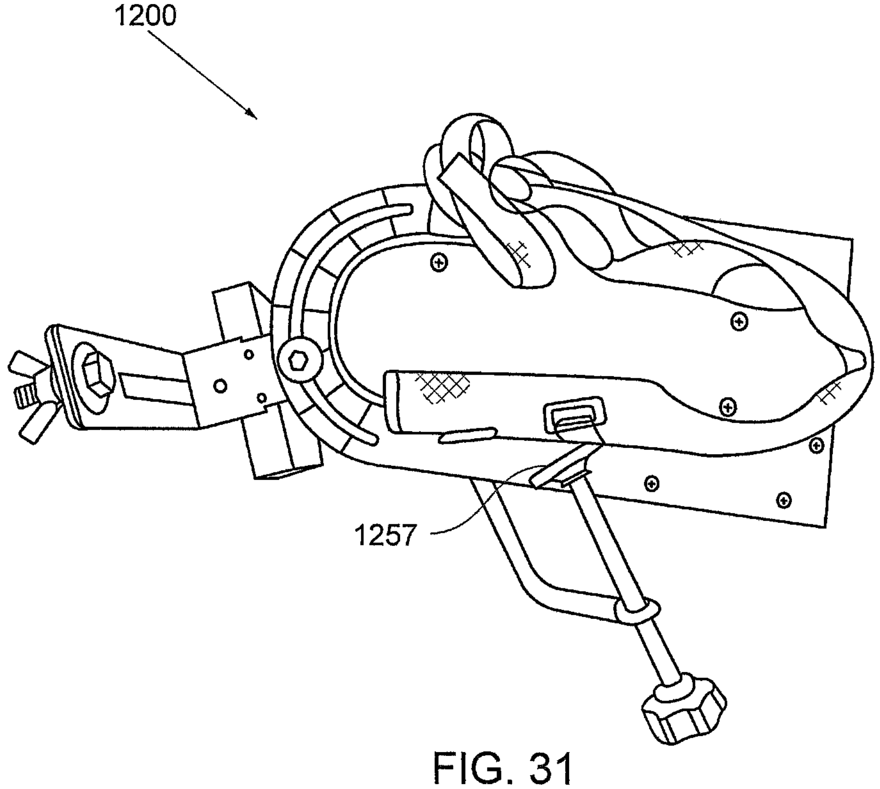
FIG. 31 illustrates a top perspective view of the traction apparatus of FIG. 30.

FIGS. 30-31 show a traction apparatus 1200 of the present invention, which may be constructed the same as apparatus 1100, but may additionally include a modified C-clamp 1250. The bottom leg 1251 of the clamp 1250 may be received within a cylindrical member 1207, which may be a rigid member. The bottom leg 1251 may be releasably secured thereto using the wing-nut 1233, and may pivot about the rod, the same as does the arm 1231. A threaded shaft 1255 may be threadably received within the upstanding leg 1252 of the clamp 1250, and may be advanced using knob 1256 until a padded end 1257 is moved into contact against the metatarsal head of the great toe, to impart a lateral force thereat. The lateral force applied by the padded end 1257 of the threaded shaft 1255 may work in combination with the force applied by the toe trap at the adduction angle provided by the particular angular orientation of the arm 1231.

Figure 32:
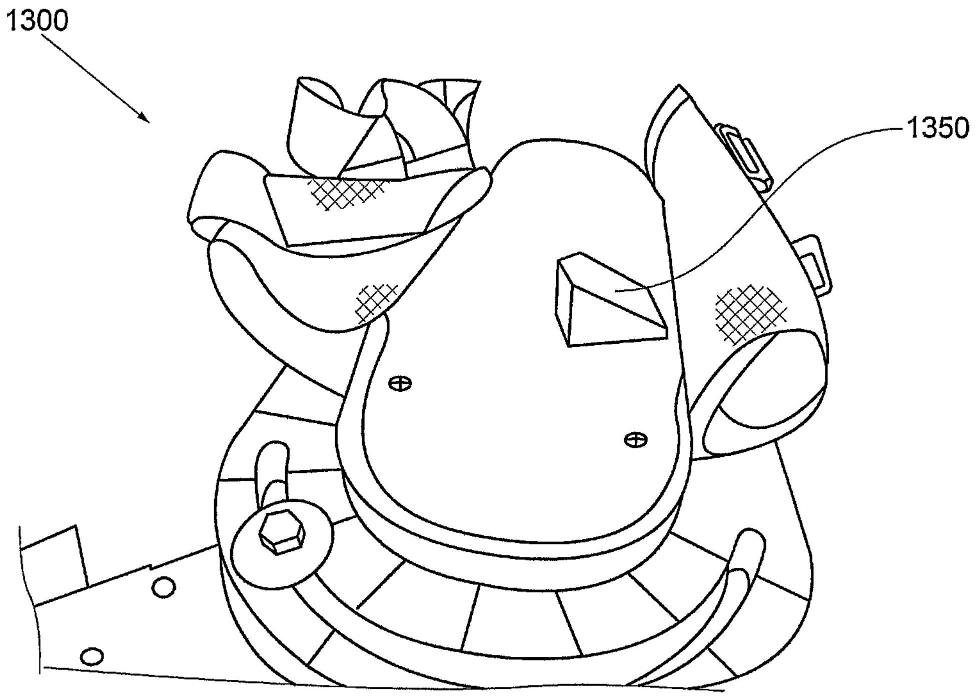
FIG. 32 illustrates a front perspective view of an alternate embodiment of the traction apparatus of FIG. 30, which includes a block that is releasably securable to the sole of the shoe, and has a vertical surface that may be suitably positioned to impart a lateral force to the head of the first Metatarsal bone.
Figure 33:
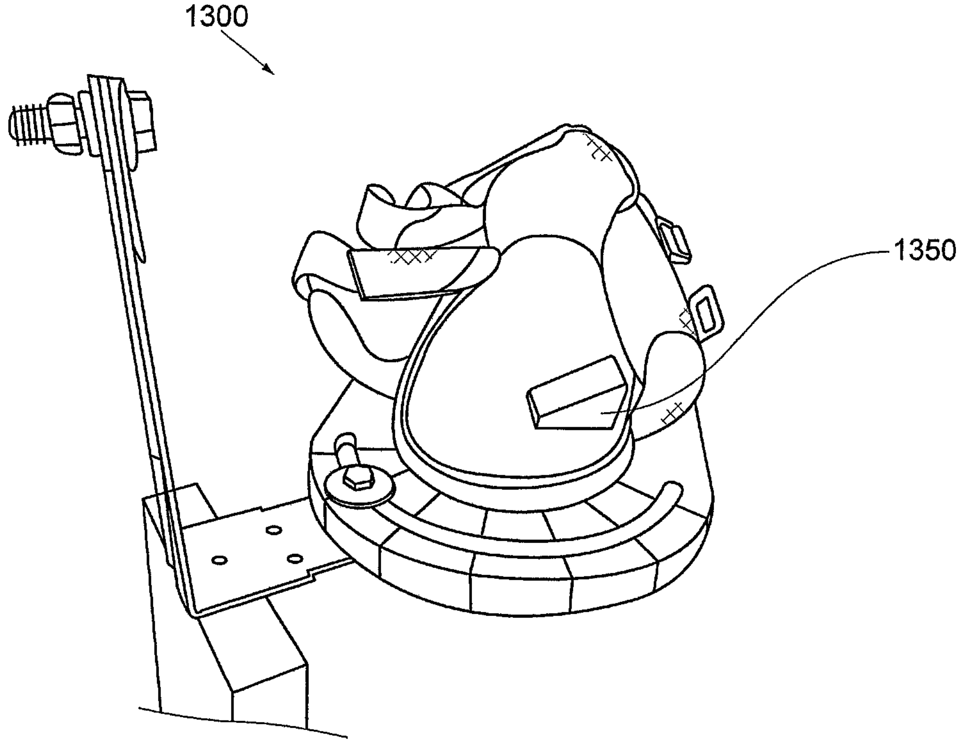
FIG. 33 is the front perspective view of FIG. 32, but showing the block rotated 180 degrees so that an angled surface thereon may be used to impart rotation to the proximal phalangeal bone of the great toe.

FIGS. 32-33 show a traction apparatus 1300 of the present invention, which may be constructed to operate similar to apparatus 1200, and may include a block 1350 that is configured to be selectively positioned with respect to the sole of the shoe (which may be oversized). The block 1350 may be padded and may be made of a high density plastic. As seen in FIG. 32, the block 1350 may be shaped to include a vertical surface and an angled surface. The vertical surface, as positioned in FIG. 32, may be used to impart a lateral force upon the head of the first metatarsal bone. The block 1350 is shown rotated 180 degrees in FIG. 33 and repositioned, so that the angled surface may be used to impart rotation to the proximal phalangeal bone of the great toe, which may rest thereon, and may augment use of the clamp, which is not shown therein. An additional strap may be used across the top of the shoe, where the block is positioned.

Figure 34:
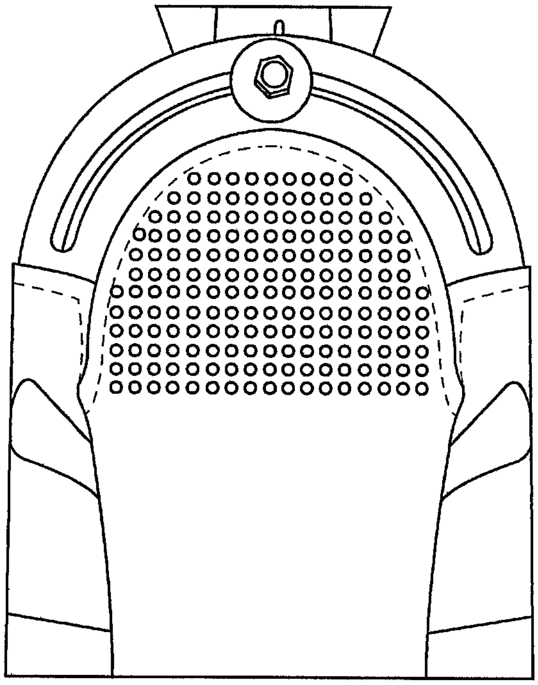
FIG. 34 is a top view of the sole of the shoe of the traction apparatus of FIGS. 33-33, showing a pegboard or area for application of Velcro that may be used to selectively position the block thereon.

The positioning of the block 1350 may be accomplished by having one or more pegs protrude from the bottom of the block, which may be received within one or more of a plurality of corresponding openings formed in a "pegboard" in roughly the front one-third of the sole of the shoe, as seen in FIG. 34. To permit greater freedom and flexibility with respect to the positioning of the block 1350, hook and loop fastening materials (i.e., Velcro®) may be used on the bottom of the block and on the sole of the shoe, instead of the peg and pegboard.

The examples and descriptions provided merely illustrate several embodiments of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

Accordingly, the breadth and scope of the present disclosure should not be limited by any of the above-described example embodiments, but should be defined only in accordance with the following claims and their equivalents.

The invention claimed is:

1. An apparatus configured to treat a bunion, said apparatus comprising:

a cable;

means for releasably securing a first end of said cable to at least a distal phalange of a digit of a patient's foot;

a shoe portion;

means for applying a specific amount of tension to said cable;

a support bracket, said support bracket comprising a first portion and a second portion, a proximal end of said first portion of said support bracket being mounted to pivot with respect to said shoe portion at a pivot axis, to reorient the specific amount of tension in said cable to an adduction angle of said cable with respect to an axial direction of said shoe portion, said first portion of said support bracket configured to extend substantially perpendicular to said pivot axis, and said second portion of said support bracket configured to extend away from a distal end of said first portion and to terminate at an elevated position with respect to said shoe portion;

an adjustment member, said adjustment member mounted to slide relative to said second portion, to adjust a dorsiflexion angle provided by said cable independent of said adduction angle; wherein a portion of said cable is supported by said adjustment member;

means for releasably securing said first portion of said support bracket with respect to said shoe portion, at least at a first pivot position for providing the specific amount of tension at an adduction angle of zero degrees, and at least at a second pivot position configured to provide the specific amount of tension at a non-zero-degree adduction angle;

means for releasably securing said adjustment member with respect to said second portion of said support bracket at a first position for providing a dorsiflexion angle of zero degrees for said cable, and at least at a first elevated position for providing the specific amount of tension at a non-zero-degree dorsiflexion angle; and means for securing said shoe portion to the foot of the patient for countering the specific amount of tension in said cable with respect to said non-zero-degree adduction angle and for countering the specific amount of tension in said cable with respect to said non-zero-degree dorsiflexion angle, for repositioning of only the digit of the patient's foot with respect to said shoe portion.

2. The apparatus according to claim 1, further comprising: a platform, said platform configured to elevate said shoe portion above a floor surface.

3. The apparatus according to claim 2, wherein said platform comprises one or more flanges, said one or more flanges being configured to elevate said shoe portion above the floor surface.

4. The apparatus according to claim 3, wherein at least said means for applying the specific amount of tension is positioned between said shoe portion and the floor surface.

5. The apparatus according to claim 4, further comprising a meter, said meter configured to indicate the specific amount of tension in said cable.

* * * * *